US009403828B2

(12) United States Patent
Chiosis

(10) Patent No.: US 9,403,828 B2
(45) Date of Patent: *Aug. 2, 2016

(54) SMALL-MOLECULE HSP90 INHIBITORS

(75) Inventor: Gabriela Chiosis, New York, NY (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 691 days.

This patent is subject to a terminal disclaimer.

(21) Appl. No.: 13/176,903

(22) Filed: Jul. 6, 2011

(65) Prior Publication Data

US 2011/0312980 A1    Dec. 22, 2011

Related U.S. Application Data

(63) Continuation-in-part of application No. 12/939,807, filed on Nov. 4, 2010, now Pat. No. 8,703,942, which is a continuation of application No. 11/814,506, filed as application No. PCT/US2006/003676 on Feb. 1, 2006, now Pat. No. 7,834,181.

(60) Provisional application No. 60/649,322, filed on Feb. 1, 2005.

(51) Int. Cl.
*C07D 473/34* (2006.01)

(52) U.S. Cl.
CPC .................... *C07D 473/34* (2013.01)

(58) Field of Classification Search
CPC ................................................ C07D 473/34
USPC ........................................................ 544/276
See application file for complete search history.

(56) References Cited

U.S. PATENT DOCUMENTS

| | | | |
|---|---|---|---|
| 4,059,655 A | 11/1977 | Crano | |
| 4,248,753 A | 2/1981 | Buchwalter et al. | |
| 4,503,145 A | 3/1985 | Katsuyama et al. | |
| 4,708,984 A | 11/1987 | Forgione et al. | |
| 5,349,023 A | 9/1994 | Ikeda et al. | |
| 5,488,138 A | 1/1996 | Nitta et al. | |
| 5,665,852 A | 9/1997 | Singh et al. | |
| 6,093,527 A | 7/2000 | Kagawa et al. | |
| 6,653,482 B2 | 11/2003 | Hollingsworth et al. | |
| 7,241,890 B2 | 7/2007 | Kasibhatla et al. | |
| 7,439,359 B2 | 10/2008 | Chiosis et al. | |
| 7,595,401 B2 | 9/2009 | Bajji et al. | |
| 7,834,181 B2 | 11/2010 | Chiosis et al. | |
| 8,217,050 B2 | 7/2012 | Moffat et al. | |
| 8,703,942 B2 | 4/2014 | Chiosis et al. | |
| 2004/0102458 A1 | 5/2004 | Chiosis et al. | |
| 2005/0049263 A1 | 3/2005 | Kasibhatla et al. | |
| 2007/0299258 A1 | 12/2007 | Bajji et al. | |
| 2008/0096903 A1 | 4/2008 | Chen et al. | |
| 2008/0221132 A1 | 9/2008 | Cai et al. | |
| 2008/0234297 A1 | 9/2008 | Qian et al. | |
| 2008/0234314 A1 | 9/2008 | Cai et al. | |
| 2009/0298857 A1 | 12/2009 | Chiosis et al. | |
| 2009/0312319 A1 | 12/2009 | Ren et al. | |
| 2010/0292255 A1 | 11/2010 | Bajji et al. | |
| 2011/0312980 A1 | 12/2011 | Chiosis | |
| 2012/0208806 A1 | 8/2012 | Chiosis et al. | |
| 2014/0045867 A1 | 2/2014 | Taldone et al. | |
| 2014/0088121 A1 | 3/2014 | Sun et al. | |
| 2014/0227183 A1 | 8/2014 | Chiosis et al. | |
| 2014/0378452 A1 | 12/2014 | Chiosis | |

FOREIGN PATENT DOCUMENTS

| | | |
|---|---|---|
| WO | 9632480 | 10/1996 |
| WO | 9640789 | 12/1996 |
| WO | 9704801 | 2/1997 |
| WO | 0236075 | 5/2002 |
| WO | 03037860 | 5/2003 |
| WO | 2005012482 | 2/2005 |
| WO | WO-2006/084030 A2 | 8/2006 |
| WO | 2006130469 A1 | 12/2006 |
| WO | 2007014323 A2 | 2/2007 |
| WO | 2007117466 A1 | 10/2007 |
| WO | 2008013985 A2 | 1/2008 |
| WO | WO-2008/005937 A2 | 1/2008 |
| WO | 2008056120 A1 | 5/2008 |
| WO | 2008070472 A2 | 6/2008 |
| WO | 2009007399 A1 | 1/2009 |
| WO | 2009042646 A1 | 4/2009 |
| WO | 2009065035 A1 | 5/2009 |
| WO | WO-2011/044394 A1 | 4/2011 |
| WO | WO-2012/138894 A1 | 10/2012 |
| WO | WO-2012/138896 A1 | 10/2012 |

OTHER PUBLICATIONS

American Cancer Society: Fluorouracil (5-FU). May 9, 2012. <http://www.cancer.org/treatment/treatmentsandsideeffects/guidetocancerdrugs/fluorouracil>.*
Eaker, Charles. Theoret. Chim. Acta (Berl.) 40, 113-118 (1875).*
Encyclopedia Britanica. "oxide." Encyclopaedia Britannica. Encyclopaedia Britannica Online Academic Edition. Encyclopædia Britannica Inc., 2014. Web. Jul. 1, 2014 <http://www.britannica.com/EBchecked/topic/436674/oxide>.*
Wright, Lisa. Chemistry & Biology vol. 11 (2004) 775-785.*
Wermuth, Camille. Molecular Variations Based on Isoteric Replacements. The Practice of Medicinal Chemistry. Academic Press, 1996. pp. 203-237.*
Bull, Elizabeth et al. "Enhanced Tumor Cell Radiosensitivity and Abrogation of G2 and S Phase Arrest by the Hsp90 Inhibitor 17-(Dimethylaminoethylamino)-17-demethoxygeldanamycin", Clinical Cancer Research, 2004, pp. 8077-8084, vol. 10.
Chiosis, Gabriela et al. "Development of a Purine-Scaffold Novel Class of Hsp90 Binders that Inhibit the Proliferation of Cancer Cells and Induce the Degradation of Her2 Tyrosine Kinase", Bioorganic & Medicinal Chemistry, Nov. 2002, pp. 3555-3564, vol. 10, Issue 11.
He, Huazhong et al. "Identification of Potent Water Soluble Purine-Scaffold Inhibitors of the Heat Shock Protein 90" J. Med. Chem., 2006, pp. 381-390, vol. 49.

(Continued)

*Primary Examiner* — Golam M M Shameem
*Assistant Examiner* — Laura Daniel
(74) *Attorney, Agent, or Firm* — Choate, Hall & Stewart LLP; John P. Rearick; Gang Wang

(57) ABSTRACT

Purine scaffold Hsp90 inhibitors are useful in therapeutic applications and as radioimaging ligands.

45 Claims, 20 Drawing Sheets

(56) References Cited

OTHER PUBLICATIONS

Llauger, Laura et al. "Synthesis of 8-arylsulfoxyl/sulfonyl adenines", Tetrahedron Letters, Dec. 20, 2004, pp. 9594-9552, vol. 45, Issue 52.
Llauger, Laura et el. "Evaluation of 8-Arylsulfanyl, 8-Arylsulfoxy, and 8-Arylsulfonyl Adenine Derivatives as Inhibitors of the Heat Shock Protein 90", J. Med. Chem., Mar. 25, 2005, pp. 2892-2905, vol. 48, Issue 8.
Lucas, Brian et al. "Facile Synthesis of a Library of 9-Alkyl-8-benzyl-9H-purin-6-ylamine Derivatives", J. Comb Chem., Sep. 21, 2001, pp. 518-520, vol. 3.
Russell, Jeffery et al. "Enhanced Cell Killing Induced by the Combination of Radiation and the Heat Shock Protein 90 Inhibitor 17-Ally;amino-17-Demethoxygeldanamycin: A multitarget Approach to Radiosensitization" Clinical Cancer Research, 2003, pp. 3749-3755, vol. 9.
Author Not Known, Hachk's Chemical Dictionary (American and British usage). Revised and edited by Julius Grant. Third Edition. The Blakiston Company, Philadelphia, p. 18 (1944).
Author Not Known, Memidex Dictionary entry: "heteroatom," Memidex, Free online dictionary/thesaurus, 3 pages <http://www.memidex.com/heteroatom> last accessed Mar. 31, 2015.
Author Not Known, The Merck Index: An Encyclopedia of Chemicals, Drugs and Biologicals, Eleventh Edition, p. 1523 (1989).
Barhate, N. et al., Simple and Practical Halogenation of Arenes, Alkenes and Alkynes with Hydrohalic Acid/H2O2 (or TBHP), Tetrahedron, 55:11127-42 (1999).
Bates, C.G. et al., A general method for the formation of aryl-sulfur bonds using copper(I) catalysts, Org. Lett., 4(16):2803-6 (2002).
Biamonte, M.A. et al., Preparation of 8-(Arylsulfanyl) adenines with Diazonium Salts under Mild, Aerobic Conditions, Journal of Organic Chemistry, 70:717-720 (2005).
Camaioni, E. et al., New substituted 9-alkylpurines as adenosine receptor ligands, Bioorg. Med. Chem., 6(5):523-33 (1998).
Castanet, A-S. et al., Mild and regioselective iodination of electron-rich aromatics with N-iodosuccinimide and catalytic trifluoroacetic acid, Tetrahedron Letters, 43:5047-8 (2002).
Chien, T-C. et al., Nuecleoside VII: 1 Synthesis of N-Triphenylphosphoranylidene Nucleosides by Mitsunobu Reaction. A Novel Protecting Group for Primary Amines of Nucleosides, Tetrahedron Letters, 36(43):7881-4 (1995).
Chiosis, G. et al., A small molecule designed to bind to the adenine nucleotide pocket of Hsp90 causes Her2 degradation and the growth arrest and differentiation of breast cancer cells, Chem. Biol., 8(3):289-99 (2001).
Chiosis, G. et al., Development of purine-scaffold small molecule inhibitors of Hsp90, Curr. Cancer Drug Targets, 3(5):371-6 (2003).
Dymock, B. et al., Adenine derived inhibitors of the molecular chaperone HSP90-SAR explained through multiple X-ray structures, Bioorg. Med. Chem. Lett., 14(2):325-8 (2004).
Fukuhara, T. et al., A Facile Preparation of Fluoropyridines from Aminopyridines via Diazotization and Fluorodediazoniation in HF or HF-Pyridine Solutions, Journal of Fluorine Chemistry, 38:435-8 (1988).
Goedert, M. et al., Epitope mapping of monoclonal antibodies to the paired helical filaments of Alzheimer's disease: identification of phosphorylation sites in tau protein, Biochem J., 301 (Pt 3):871-7 (1994).
He, H. et al., General method for the synthesis of 8-arylsulfanyl adenine derivatives, J. Org. Chem., 69(9):3230-2 (2004).
Huezo, H. et al., Microtiter cell-based assay for detection of agents that alter cellular levels of Her2 and EGFR, Chem. Biol., 10(7):629-34 (2003).
International Search Report for PCT/US2006/003676, 3 pages (Nov. 30, 2006).
Kamal, A. et al., Therapeutic and diagnostic implications of Hsp90 activation, Trends Mol. Med., 10(6):283-90 (2004).
Kelland, L.R. et al., DT-Diaphorase expression and tumor cell sensitivity to 17-allylamino, 17-demethoxygeldanamycin, an inhibitor of heat shock protein 90, J. Natl. Cancer Inst., 91(22):1940-9 (1999).
Kim, J. et al., Development of a fluorescence polarization assay for the molecular chaperone Hsp90, J. Biomol. Screen., 9(5):375-81 (2004).

Kropp, P. et al., Surface-Mediated Reactions. 8. Oxidation of Sulfides and Sulfoxides with tert-butyl Hydroperoxide and OXONE1, J. Am. Chem. Soc., 122:4280-4285 (2000).
Kwong, F.Y. and Buchwald, S.L., A general, efficient, and inexpensive catalyst system for the coupling of aryl iodides and thiols, Org. Lett., 4(20):3517-20 (2002).
Laxer, A. et al., ((15)N(5))-labeled adenine derivatives: synthesis and studies of tautomerism by (15)N NMR spectroscopy and theoretical calculations, J. Org. Chem., 66(16):5463-81 (2001).
Leuckart, J. et al., Leuckart Thiophenol Reaction, Chem., 41:179 (1890).
Leuckart, R., Leuckart Thiophenol Reaction, J. Prakt. Chem., 41:179, DrugFuture.com, 1 page (1890) <http://www.drugfuture.com/organicnamereactions/ONR235.htm> last accessed on Jun. 11, 2012.
Llauger, L. et al., Evaluation of 8-Arylsulfanyl, 8-Arylsulfoxyl, and 8-Arylsulfonyl Adenine Derivatives as Inhibitors of the Heat Shock Protein 90, J. Med.Chem., 48(8):2892-2905 (2005).
Llauger-Bufi, L. et al., Synthesis of novel fluorescent probes for the molecular chaperone Hsp90, Bioorg. Med. Chem. Lett., 13(22):3975-8 (2003).
Maloney, A. and Workman, P., HSP90 as a new therapeutic target for cancer therapy: the story unfolds, Expert Opin. Biol. Ther., 2(1):3-24 (2002).
Mimnaugh, E.G. et al., Polyubiquitination and proteasomal degradation of the p185c-erbB-2 receptor protein-tyrosine kinase induced by geldanamycin, J. Biol. Chem., 271(37):22796-801 (1996).
Mitsunobu, O., The Use of Diethyl Azodicarboxylate and Triphenylphosphine in Synthesis and Transformation of Natural Products, Synthesis, 1-28 (1981).
Mosser, D.D. and Morimoto, R.I., Molecular chaperones and the stress of oncogenesis, Oncogene, 23(16):2907-18 (2004).
Neckers, L., Hsp90 inhibitors as novel cancer chemotherapeutic agents, Trends Mol. Med., 8(4 Suppl):S55-61 (2002).
Offer, J. et al., Extending synthetic access to proteins with a removable acyl transfer auxiliary, J. Am. Chem. Soc., 124(17):4642-6 (2002).
Roberge, M. et al., Cell-based screen for antimitotic agents and identification of analogues of rhizoxin, eleutherobin, and paclitaxel in natural extracts, Cancer Res., 60(18):5052-8 (2000).
Sausville, E.A. et al., Clinical development of 17-allylamino, 17-demethoxygeldanamycin, Curr. Cancer Drug Targets., 3(5):377-83 (2003).
Sigel, H., Acid-base properties of purine residues and the effect of metal ions: Quantification of rare nucleobase tautomers, Pure Appl. Chem., 76(10):1869-1886 (2004).
Soga, S. et al., Development of radicicol analogues, Curr. Cancer Drug Targets, 3(5):359-69 (2003).
Solit, D.B. et al., Phase 1 pharmacokinetic and pharmacodynamic trial of docetaxel and 17AAG (17-allylamino-17-demethoxygeldanamycin, Journal of Clinical Oncology, 22(14S): 3032 (2004).
Srethapakdi, M. et al., Inhibition of Hsp90 function by ansamycins causes retinoblastoma gene product-dependent G1 arrest, Cancer Res., 60(14):3940-6 (2000).
Tarbell, T.S. et al., m-Thiocresol, Organic Syntheses, Collection, 27:81 (1947).
Thompson, A. et al., Synthesis of 7-substituted 3 aryl-1,6-naphthyridin-2-amines and 7-substituted 3-aryl-1,6-naphthyridin-2(1H)-ones via diazotization of 3-aryl-1,6-naphthyridine-2,7diamines, J. Chem. Soc., Perkin Trans. 1, pp. 1843-1852 (2000).
Thornber, C.W., Isosterism and molecular modification in drug design, Chem. Soc. Rev., 8.4:563-580 (1979).
Tipson, R., On Esters of p-Toluenesulfonic Acid, Contribution from the Department of Research in Pure Chemistry, Mellon Institute of Industrial Research, pp. 235-241 (1944).
Vanallan, J.A. et al., 2-mercaptobenzimidazole, Organic Syntheses, Coll., 4:569 (1963).
Vilenchik, M., et al., Targeting wide-range oncogenic transformation via PU24FCI, a specific inhibitor of tumor Hsp90, Chem. Biol., 11(6):787-97 (2004).
Vincent, I. et al., Mitotic phosphoepitopes precede paired helical filaments in Alzheimer's disease, Neurobiol. Aging., 19(4):287-96 (1998).
Wegele, H. et al., Hsp70 and Hsp90—a relay team for protein folding, Rev. Physiol. Biochem. Pharmacol., 151:1-44 (2004).
Written Opinion for PCT/US2006/003676, 7 pages (Nov. 30, 2006).

* cited by examiner

PU-H58

PU-H64

PU-DZ2

PU-DZ3

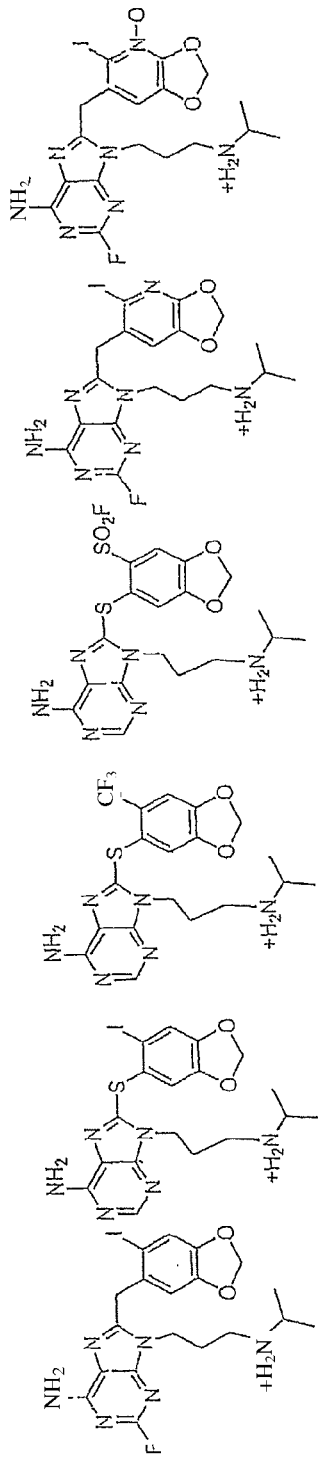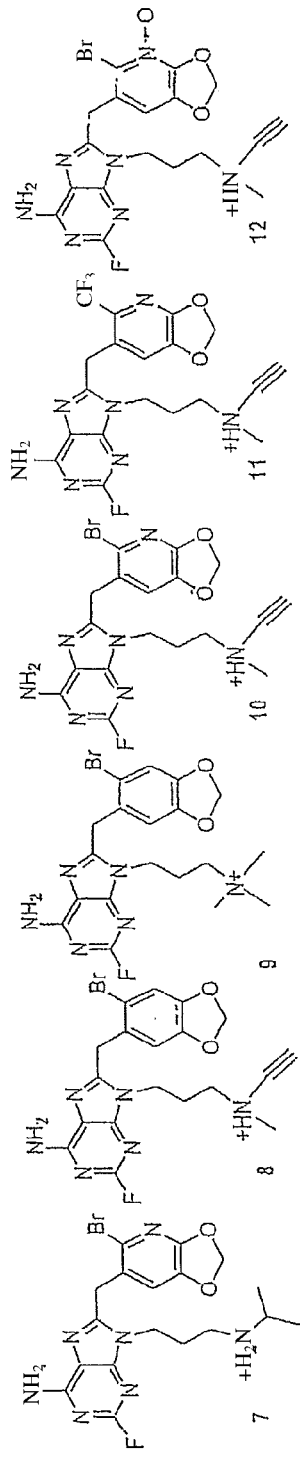

Scheme 1ᵃ

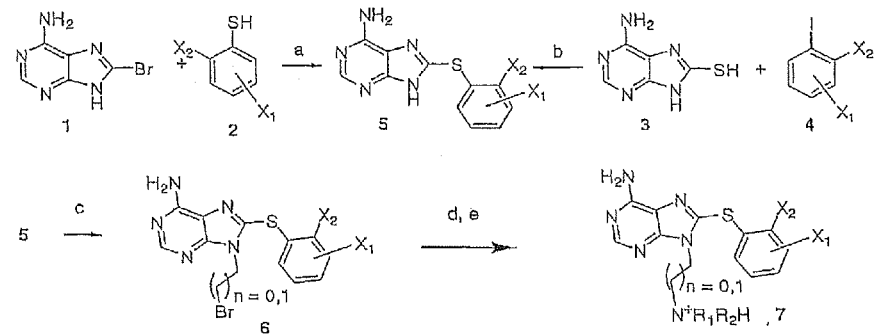

ᵃ Reagents and conditions: (a) K₂CO₃, DMF, 90-120°C; (b) NaOt-Bu, K₂CO₃ or Na₃PO₄, neocuproine, CuI, DMF, 110°C; (c) Br(CH₂)₂₋₃OH, PPh₃, DBAD, toluene·CH₂Cl₂, rt, 30min; (d) R₁R₂NH, K₂CO₃, DMF, 50°C, (e) H₃PO₄ – ether precipitate

Fig. 5A

Scheme 2ᵃ

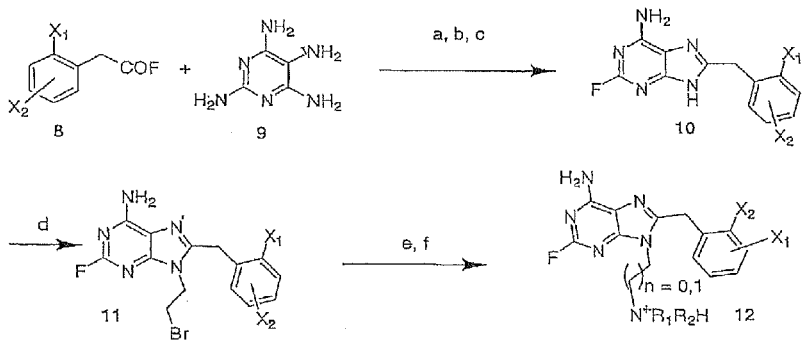

ᵃ Reagents and conditions: (a) K₂CO₃, DMAP, DMF, 120°C, 2h; (b) NaOMe, 105°C, 4h, MeOH/ i-BuOH 1:1; (c) HF-pyridine, NaNO₂, rt, 1h; (d) Br(CH₂)₂₋₃OH, PPh₃, DBAD, toluene·CH₂Cl₂, rt, 30min; (e) R₁R₂NH, K₂CO₃, DMF, 50°C; (f) H₃PO₄ – ether precipitate

Fig. 5B

Scheme 3

<sup>a</sup> Reagents and conditions. (a) CS₂, NaHCO₃, H₂O/EtOH, reflux, 97%; (b) ArI, NaO/-Bu, CuI, ethylene glycol, 130°C, 60%; (c) HF-pyridine, NaNO₂, -40 C to rt, 15-20%; (d) ROH, PPh₃, DBAD, toluene.CH₂Cl₂, rt, 50%; (e) ROTs, Cs₂CO₃, DMF, 80 C, 50%; (f) HCl, t-BuOOH, 1,4-dioxane or i-PrOH, 80°C, 20-70%; (g) NBS, DMF, rt, 80%; (h) ArSH, K₂CO₃, DMF, 130°C, 85%. Method E: a, b, c, d; Method F: a, b, c, d, f; Method G: a, b, e, f, e; Method H: e, g, h Scheme 4

[a] Reagents and conditions: (a) OXONE®, alumina, CH$_2$Cl$_2$, rt, 35-70%. (b) AcOH, EtOH, reflux, 60-70%; (c) HCl, t-BuOOH, MeOH, 80°C, 43%.

SMALL-MOLECULE HSP90 INHIBITORS

STATEMENT OF RELATED CASES

This application is a continuation-in-part of U.S. application Ser. No. 12/939,807, filed Nov. 4, 2010, which is a continuation of U.S. application Ser. No. 11/814,506 filed on Jul. 23, 2007, now U.S. Pat. No. 7,834,181, which is a national phase of PCT/US2006/003676, filed Feb. 1, 2006, which claims the benefit of U.S. Provisional Patent Application No. 60/649,322 filed Feb. 1, 2005, all of which are incorporated herein by reference in their entirety.

FIELD OF THE INVENTION

This application relates to compounds effective as inhibitors of Hsp90, and to the use of such molecules in therapeutic applications. The molecules of the invention are useful in therapeutic applications and as radioimaging ligands.

BACKGROUND OF THE INVENTION

The chaperone heat shock protein 90 (Hsp90) is an emerging target in cancer treatment due to its important roles in maintaining transformation and in increasing the survival and growth potential of cancer cells. Hsp90 function is regulated by a pocket in the N-terminal region of the protein that binds and hydrolyzes ATP. Occupancy of this pocket by high affinity ligands prevents the dissociation of Hsp90 client proteins from the chaperone complex and as a consequence, the trapped proteins do not achieve their mature functional conformation and are degraded by the proteasome. Protein clients of Hsp90 are mostly kinases, steroid receptors and transcriptional factors involved in driving multistep-malignancy and in addition, mutated oncogenic proteins required for the transformed phenotype. Examples include Her2, Raf-1, Akt, Cdk4, cMet, mutant p53, ER, AR, mutant BRaf, Bcr-Abl, Flt-3, Polo-I kinase, HQF-I alpha and hTERT. Degradation of these proteins by Hsp90 inhibitors leads to cell-specific growth arrest and apoptosis in cancer cells in culture, and to tumor growth inhibition or regression in animal models. One such inhibitor, 17-allyl-amino-desmethoxy-geldanamycin (17 AAG, FIG. 1A) has entered clinical trials in cancer patients in the US and UK and has shown early evidence of therapeutic activity when administered alone or in combination with docetaxel. Despite these early promising results, 17AAG has several potential limitations. Most prominent are its limited solubility and cumbersome formulation. It also exhibits dose and schedule dependent liver toxicity believed to be caused by the benzoquinone functionality. Radicicol (RD, FIG. 1B) a structurally unrelated natural product, has biological activity similar to that of 17AAG but is not hepatotoxic, yet no derivative of this class has made it into clinic.

Making use of the peculiar bent shape of Hsp90 inhibitors and of existent Hsp90 crystal data, purine-scaffold derivatives with Hsp90 inhibitory activities have been designed. PCT Application No. WO02/36075, which is incorporated herein by reference identified a generalized structure for purine scaffold inhibitor class of compounds with the formula:

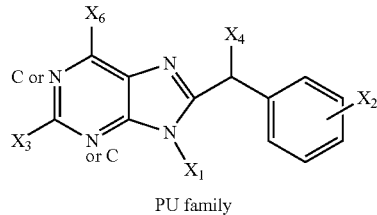

PU family

The first synthesized derivative of this class, PU3 (FIG. 1C), bound Hsp90 with moderate affinity and elicited cellular effects that mimic 17AAG addition. Preliminary efforts focused at improving the potency of this agent have mostly focused on modifying the left side of the scaffold and have led to the synthesis of several compounds with improved activity in both biochemical and cellular assays. One such compound, PU24FC1 (FIG. 1D) is a potent and selective inhibitor of tumor Hsp90 and exhibits anti-tumor activities in both in vitro and in vivo models of cancer. Other purine-scaffold compounds with higher potency over PU24FC1 in in vitro models of cancer have subsequently been disclosed. (See, PCT Patent Publication No. WO03/037860, which is incorporated herein by reference.) Although a significant number of derivatives has been created by these combined efforts, the nature and position of substituents on the right side aryl moiety ($X_2$ in the structure above) and nature of the linker between the two rings have not been sufficiently investigated. The present invention provides a class of Hsp90 inhibitors with enhanced activity as compared to previously known compounds and a class of inhibitors with differential selectivity and activity for Rb normal versus Rb defective cells.

SUMMARY OF THE INVENTION

In accordance with the present invention, Hsp90 inhibitors are provided having the formula:

left side-linker–right side wherein
(a) the left side has the formula of the left side in the PU family of purine scaffold inhibitor class of compounds:

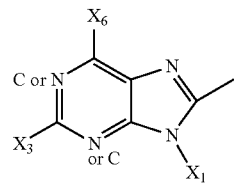

in which:
  $X_6$ is $NH_2$;
  $X_3$ is hydrogen or halogen, for example F or Cl or Br; and
  $X_1$ is hydrogen,
    a $C_1$ to $C_{10}$ alkyl, alkenyl, or alkynyl group,
    a saturated or unsaturated moiety containing up to 10 carbon atoms and at least one heteroatom, or
    a targeting or labeling moiety connected to the left side at N9,
(b) the linker is selected from the group consisting of $CH_2$, O, NH and S, and
(c) the right side has the formula:

-six-membered aryl ring-$(X_2)(X_4)(X_5)$ wherein
  $X_2$ is disposed at the two-position of the aryl ring and is halogen, alkyl, alkoxy, halogenated alkoxy, hydroxyalkyl, pyrollyl, optionally substituted aryloxy, alkylamino, dialkylamino, carbamyl, amido, alkylamido dialkylamido, acylamino, alkylsulfonylamido, trihalomethoxy, trihalocarbon, thioalkyl, $SO_2$-alkyl, COO-alkyl, $NH_2$, OH, CN, $SO_2X_5$, $NO_2$, NO, C=S—$R_2$, $NSO_2X_5$, C=$OR_2$, where $X_5$ is F, $NH_2$, alkyl or H, and $R_2$ is alkyl, $NH_2$, NH-alkyl or O-alkyl; and $X_4$ and $X_5$, which may be the same or different, are disposed at the 4 and 5 positions of the aryl ring, wherein $X_4$ and $X_5$ are selected from halogen, alkyl, alkoxy, halogenated alkoxy, hydroxyalkyl, pyrollyl, optionally substituted aryloxy, alkylamino, dialkylamino, carbamyl, amido, alkylamido dialkylamido, acylamino, alkylsulfonylamido, trihalomethoxy, trihalocarbon, thioalkyl, $SO_2$.alkyl, COO-alkyl, $NH_2$ OH, CN, $SO_2X_5$, $NO_2$, NO, C=$SR_2$ $NSO_2X_5$, C=$OR_2$, where $X_5$ is F, NH2, alkyl or H, and $R_2$ is alkyl, $NH_2$, NH-alkyl or O-alkyl, $C_1$ to $C_6$ alkyl or alkoxy; or wherein $X_4$ and $X_5$ taken together have the formula —O—$(CH_2)_n$—O—, wherein n is an integer from 0 to 2.

The Hsp90 inhibitors can be used for therapeutic application in the treatment of cancer and other conditions where the cells depend on hsp90 activity for cell growth or maintenance. Radiolabeled Hsp90 inhibitors of the invention are useful as radiotracers for imaging tumors that express Hsp90.

BRIEF DESCRIPTION OF THE DRAWINGS

FIGS. 5A-D shows synthetic schemes for making compositions in accordance with the invention.

DETAILED DESCRIPTION OF THE INVENTION

Compositions of the Invention

Figure 1A:
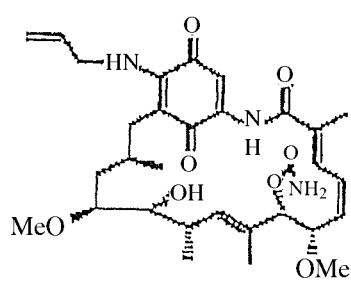
FIGS. 1A and B shows the structure of prior art Hsp90 inhibitors 17-AAG and radicicol.
Figure 1B:
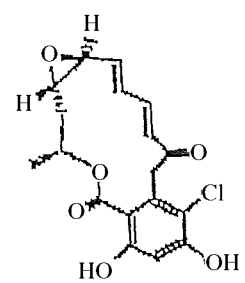
FIGS. 1C and 1D shows the structure of prior art purine-scaffold Hsp90 inhibitor PU3 and PU24FC1.
Figure 1C:
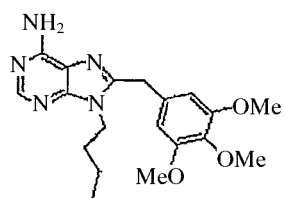

The present application provides small molecule Hsp90 inhibitors that are purine-scaffold derivatives of adenine with the general structure:

left side-linker–right side wherein
(a) the left side has the formula of the left side in the PU family of purine scaffold inhibitor class of compounds:

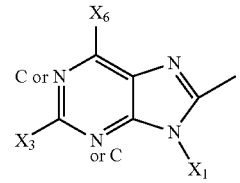

in which:
$X_6$ is $NH_2$;
$X_3$ is hydrogen or halogen, for example F or Cl or Br; and
$X_1$ is hydrogen,
a $C_1$ to $C_{10}$ alkyl, alkenyl, or alkynyl group,
a saturated or unsaturated moiety containing up to 10 carbon atoms and at least one heteroatom, or
a targeting or labeling moiety connected to the left side at N9, (b) the linker is selected from the group consisting of $CH_2$, O, NH and S, and (c) the right side has the formula:

-six-membered aryl ring-$(X_2)(X_4)(X_5)$ wherein
$X_2$ is disposed at the two-position of the aryl ring and is halogen, alkyl, alkoxy, halogenated alkoxy, hydroxyalkyl, pyrollyl, optionally substituted aryloxy, alkylamino, dialkylamino, carbamyl, amido, alkylamido dialkylamido, acylamino, alkylsulfonylamido, trihalomethoxy, trihalocarbon, thioalkyl, $SO_2$-alkyl, COO-alkyl, $NH_2$, OH, CN, $SO_2X_5$, $NO_2$, NO, C=S $R_2$ $NSO_2X_5$, C=$OR_2$, where $X_5$ is F, $NH_2$, alkyl or H, and $R_2$ is alkyl, $NH_2$, NH-alkyl or O-alkyl; and $X_4$ and $X_5$, which may be the same or different, are disposed at the 4 and 5 positions of the aryl ring, wherein $X_4$ and $X_5$ are selected from halogen, alkyl, alkoxy, halogenated alkoxy, hydroxyalkyl, pyrollyl, optionally substituted aryloxy, alkylamino, dialkylamino, carbamyl, amido, alkylamido dialkylamido, acylamino, alkylsulfonylamido, trihalomethoxy, trihalocarbon, thioalkyl, $SO_2$.alkyl, COO-alkyl, $NH_2$ OH, CN, $SO_2X_5$, $NO_2$, NO, C=$SR_2$ $NSO_2X_5$, C=$OR_2$, where $X_5$ is F, NH2, alkyl or H, and $R_2$ is alkyl, $NH_2$, NH-alkyl or O-alkyl, $C_1$ to $C_6$ alkyl or alkoxy; or wherein $X_4$ and $X_5$ taken together have the formula —O—$(CH_2)_n$—O—, wherein n is an integer from 0 to 2.

As would be understood by persons skilled in the art, atoms named as part of the compound have an appropriate number of bonds to adjacent atoms to satisfy valency requirements for the particular atom.

In some embodiments of the invention, the left side contains two nitrogen atoms at the 1 and 3 positions.

The six-membered aryl group of the right side may be phenyl or may include one or more heteroatoms. For example, the six-membered aryl group may be a nitrogen-containing aromatic heterocycle such as pyrimidine.

In specific preferred embodiments of the composition of the invention, the groups $X_4$ and $X_5$ taken together have the formula —O—$(CH_2)_n$—O—, wherein n is an integer from 0 to 2, preferably 1 or 2. One of the oxygens is bonded at the 5'-position of the aryl ring and the other at the 4' position. In other specific embodiments of the invention, the substituents $X_1$ comprise alkoxy substituents, for example methoxy or ethoxy, at the 4' and 5'-positions of the aryl ring.

In specific embodiments of the invention, the substituent $X_2$ is a halogen.

In specific embodiments, $X_2$ is $NH_2$, alkylamino or dialkylamino.

In specific embodiments, $X_1$ is an amino alkyl moiety, optionally substituted on the amino nitrogen with one or two carbon-containing substituents selected independently from the group consisting of alkyl, alkenyl and alkynyl substituents, wherein the total number of carbons in the amino alkyl moiety is from 1 to 10.

In specific embodiments of the invention, the linker is S. In other specific embodiments of the invention, the linker is $CH_2$.

In specific embodiments of the invention, $X_1$ is a pent-4-ynyl substituent. In other specific embodiments of the invention, $X_1$ contains a heteroatom, for example nitrogen. A preferred $X_1$ group that increases the solubility of the compound relative to an otherwise identical compound in which $X_1$ is H or pent-4-ynyl is —$(CH_2)_n$—N—$R_{10}R_{11}$ or —$(CH_2)_n$—$N^+$—$R_{10}R_{11}R_{12}$, where m is 2 or 3 and where $R_{10\text{-}12}$ are independently selected from hydrogen, methyl, ethyl, ethene, ethyne, propyl, isopropyl, isobutyl, ethoxy, cyclopentyl, an alkyl group forming a 3 or 6-membered ring including the N, or a secondary or tertiary amine forming a 6-membered ring with the nitrogen. In specific examples, $R_{10}$ and $R_{11}$ are both methyl, or one of $R_{10}$ and $R_n$ is methyl and the other is ethyne. When $X_1$ contains a quaternary nitrogen, a pharmaceutically acceptable counterion is also present.

Figure 3A:
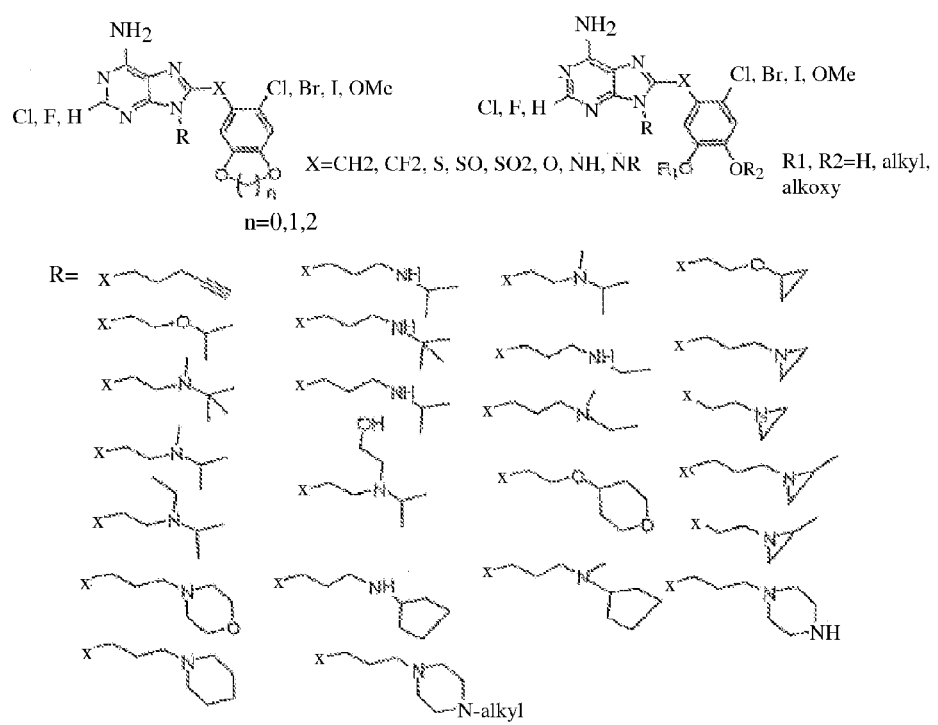
FIG. 3 A-Q shows the structures of various purine-scaffolded Hsp90 inhibitors in accordance with the present invention.

FIG. 3A shows exemplary structures in accordance with the present invention. The structures are based on one of two right side aryl substitution patterns in which the 4' and 5-substituents are either a bridging substituent or dihydroxy/alkoxy. The left side adenine has varying substituents (Cl, F or H) at the 2-position ($X_3$), and choices for the N9 substituent $X_1$ are listed. FIGS. 3 B-Q shows additional options for specific structures in accordance with the invention.

In some embodiments of the invention, $X_1$ includes a cyclic portion. In some embodiments, this cyclic portion includes one or more heteroatoms. The cyclic portion may be a three membered ring. The cycle portion may be a six membered ring.

Synthesis of Compositions in Accordance with the Invention

Synthesis of sulfur linker derivatives can be achieved using the procedures as outlined in Scheme 1 (FIG. 5A). Formation of a sulfur link between adenine and the phenyl ring (linker=S) may be obtained either by nucleophilic attack of the arylthiolate anion on 8-bromoadenine (Step a, Scheme 1) or by the copper catalyzed coupling of aryliodides with mercaptoadenine (Step b, Scheme 1). Our developed method for the formation of 8-arylsulfanyl adenine derivatives (5) from 8-mercaptoadenine (3) and aryl iodides (4) uses CuI/neocuproine as catalyst and NaOt-Bu/DMF as the base/solvent combination. The reaction occurs in anhydrous DMF at 110° C. under nitrogen to generate the products in good yields. If bromine or chlorine is present on the aryl moiety, the coupling requires milder basic condition and utilizes $Na_3PO_4$ or $K_2CO_3$ instead of NaOt-Bu. Although less attractive due to thiophenols' limited commercial availability, stench and tendency to quickly oxidize, coupling of 8-bromoadenine (1) with thiophenols in the presence of a base will also be used. When not commercially available, thiophenols can be generated by a modified Leuckart thiophenol reaction starting from the corresponding aryl amine. In a first step, aryl amines will be converted via the aryl diazonium salt to aryl xanthates which afford thiophenols on reduction with $LiAlH_4$ or on warming with a base solution. The 8-arylsulfanyl adenines 5 obtained in these coupling reactions will be further alkylated at the position 9-N with pent-4-ynyl or the corresponding -bromoalkylalcohols. Their introduction will be carried out using a Mitsunobu type reaction between the alcohol and the respective 8-arylsulfanyl adenines in toluene/$CH_2Cl_2$ to result in the corresponding 9-N-alkyl-8-arylsulfanyl adenines. Formation of the 3-N and 7-N isomers is likely to be observed (~0 to 30%), however, these byproducts will be removed by column chromatography (differences in Rf are considerable). Treatment of 5 with base and an alkylating agent tends to result in higher percentage of 3- and 7-N isomers compared to alcohol treatment under the Mitsunobu conditions. Heating these bromines with amines in DMF will generate the desired products. Phosphate salts will be further made for in vivo administration of selected compounds to improve their water solubility.

Synthesis of methylene linker derivatives can be accomplished using the precoures outlined in Scheme 2 (FIG. 5B). If the linker is methylene (linker=$CH_2$), synthesis will commence with coupling of the commercially available 2,4,5,6-tetraaminopyrimidine sulfate (9) with the acid fluoride (8) of the corresponding carboxylic acids. We have previously determined this to be the only coupling method that in our hands gives the product in high yields. Acid fluorides are generated by treating the corresponding carboxylic acids with cyanuric fluoride and pyridine in $CH_2Cl_2$. Following a quick water wash, the resulted acid fluorides are used in the next step without further purification. To make the necessary 2-chloro, bromo or iodo-4,5-derivatized phenyl acetic acids we have determined optimal reaction conditions. We have identified that treatment of 4,5-derivatized phenyl acetic acids with ICl/AcOH; NBS; or HCl/t-BuOOH gives solely ortho-iodinated; brominated; or chlorinated product, respectively in high yields. The amides resulted from the pyrimidine-acid fluoride couplings will be cyclized by heating in alcoholic NaOMe. Transformation of the C2-amino group to fluorine ($X_3$=$NH_2$ to F) will be conducted by diazotization-fluorodediazoniation of the amino derivative in HF/pyridine in the presence of $NaNO_2$ to yield the corresponding adenine derivatives 10. This reaction gives significantly higher yields over the method using $HBF_4$/iso-amyl nitrite, likely to be due at least in part to the more anhydrous nature of this solvent system which reduces the proportion of hydrolysis. Further alleviation will be conducted using the reaction sequence mentioned in Scheme 1 to result in derivatives 12.

Figure 5C:
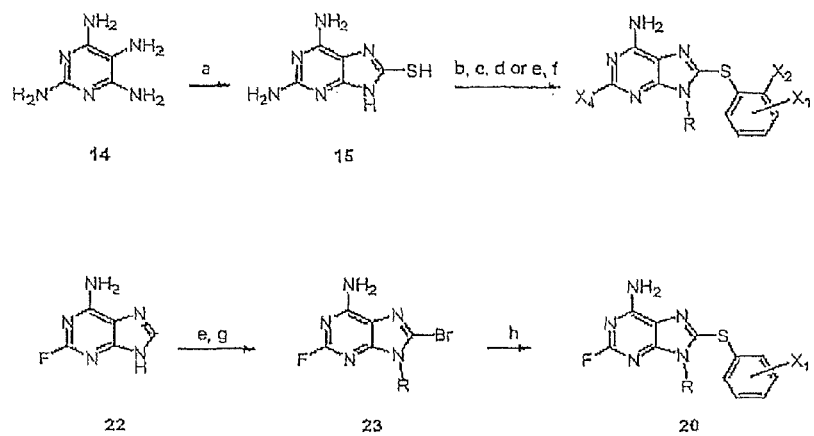

Several derivatives were prepared by the introduction of fluorine at position C2 of the adenine moiety (Scheme 3, FIG. 5C). We and others have previously determined that fluorine in this position in general increased the solubility and/or potency of the resulting purines. For the preparation of such derivatives, synthesis commenced with the condensation of the commercially available 2,4,5,6-tetraaminopyrimidine sulfate (14) with carbon disulfide in a refluxing solution of $NaHCO_3$ in aqueous EtOH.[17] The resulting 2-amino-8-mercaptoadenine (15) was further coupled with aryl iodides in the presence of NaOt-Bu and CuI in ethylene glycol to give 2-amino-8-arylsulfanyl adenines 16. The reaction did not proceed using the method published by He et al as 15 did not dissolve in DMF or most organic solvents for that matter. Unsaturated $X_1$ chains at position 9-N were introduced at this stage to result in the 2-amino-9-N-alkyl-8-arylsulfanyl adenines 17. The reaction required the use of $K_2CO_3$ or $Cs_2CO_3$ and an alkylating agent in DMF due to the poor solubility of 16 in the Mitsunobu reaction solvent. If further, introduction of chlorine at $X_2$ on the aryl moiety was desired, compounds 17 were subjected to HCl/t-BuOOH to result preferentially in ortho-chlorinated compounds (18). Transformation of the C2-amino group to fluorine ($X_4$=$NH_2$ to F)

was conducted by diazotization-fluorodediazon-iation of the amino derivative in HF/pyridine in the presence of $NaNO_2$ to yield the corresponding 2-fluoro-9-N-alkyl-8-arylsulfanyl adenine derivatives 21. This reaction gave significantly higher yields over the previously published method using $HBF_4$/iso-amyl nitrite, likely to be due at least in part to the more anhydrous nature of this solvent system which reduces the proportion of hydrolysis. Synthesis of derivatives containing both an unsaturated chain at 9-N (i.e. pent-4-ynyl) and fluorine at the C2 position of the adenine moiety ($X_3$=F) required a different strategy to avoid fluorine addition to the triple bond. Compound 16 was first subjected to introduction of fluorine at C2 to result in the corresponding 2-fluoro-8-arylsulfanyl adenine 19. Surprisingly, conducting the reaction at room temperature resulted in addition of fluorine at both C2 and C6 of the purine moiety. This problem was averted by lowering the reaction temperature to −40° C. Addition of fluorine at position C2 significantly increased the solubility of these purines in organic solvents. Thus, further alkylation could be easily conducted using the Mitsunobu reaction in toluene: $CH_2Cl_2$ to result in derivatives 20. Introduction of chlorine ($X_2$=Cl), again with HCl/t-BuOOH led to formation of 21. Alternatively, synthesis of 2-fluoro-9-N-alkyl-8-arylsulfanyl adenines 20 was started with the commercially available 2-fluoroadenine (22) (Scheme 3). This reagent was first 9-N alkylated by $Cs_2CO_3$/tosylate treatment followed by 8-bromination with N-bromosuccinimide (NBS) 19 to result in 2-fluoro-9-N-alkyl-8-bromo adenine 23. Its coupling with thiophenols generated the 2-fluoro-9-N-alkyl-8-arylsulfanyl adenines 20.

Figure 5D:
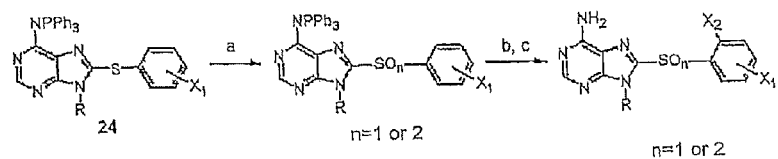

Syntheses of 8-arylsulfoxyl adenine derivatives 27 and 8-arylsulfonyl adenine derivatives 28 (Scheme 4, FIG. 5D) were previously reported by Llauger et al. Briefly, synthesis started with the preparation of Q-NH$_2$ triphenylphosphine-protected 9-N-alkyl-8-arylsulfanyl adenine derivatives 24 in a two-step (alkylation-protection) one-pot reaction from the corresponding 8-arylsulfanyl adenines 10 using the Mitsunobu conditions 13b followed by addition of an excess of PPh3 and di-tert-butyl azodicarboxylate (DBAD). Oxidation of 24 with OXONE® in the presence of alumina 22 allowed for monitoring the reaction to either sulfoxide (25) or sulfone (26). Deprotection of the C6-NH$_2$ triphenylphosphine group was conveniently conducted in refluxing AcOH/EtOH to result in good yields in the corresponding 8-arylsulfoxyl adenine derivatives 27 and 8-arylsulfonyl adenine derivatives 28. The later could be chlorinated at C2 ($X_2$=Cl) by HCl/t-BuOOH treatment to result in derivatives 29.

Using these methods, the compositions described in this application were prepared. These compositions include various compositions in accordance with the invention, as well as comparative examples.

Biological Testing

Compounds synthesized above were tested in a biochemical assay, and also in cellular assays that probe for cellular fingerprints of Hsp90 inhibition. The biochemical assay tests competitive binding of compounds to recombinant Hsp90α protein and also Hsp90 found in cell specific complexes, and uses a fluorescence polarization method. When using cell lysates instead of recombinant protein, the assay measures binding to average. Hsp90 population found in cell specific complexes. The cellular assays measure two specific biological effects observed upon addition of known Hsp90 inhibitors to cancer cells: (a) degradation of the tyrosine kinase Her224 and (b) mitotic block in Rb-defective cells.

Overexpression of the receptor tyrosine kinase Her2 in SKBr3 breast cancer cells leads to Akt activation which in turn promotes cell survival. Hsp90 uniquely stabilizes Her2 via interaction with its kinase domain and an Hsp90 inhibitor induces Her2 degradation by disrupting the Her2/Hsp90 association. We have previously reported a fast microliter immunoassay able of quantifying cellular levels of Her2 following drug treatments. This assay is used here to differentiate the Her2-degradative potential of the above synthesized purines. Hsp90 inhibitors are also known to cause cells lacking functional RB to progress normally through G1 and arrest in mitosis. Thus, another assay used here to test cellular Hsp90 inhibition relies on assessing the anti-mitotic potential of synthesized purines. The assay is a niicrotiter immunoassay and uses an antibody against a mitotically phosphorylated form of nucleolin to detect cells in mitosis. This antibody (Tg-3), originally described as a marker of Alzheimer's disease, is highly specific for mitotic cells, Tg-3 immunofluorescence being >50-fold more intense in mitotic cells than in interphase cells. In addition, the cytotoxicity of these agents against SKBr3 breast cancer cells was determined. A selected number of most active purines were also tested for possible toxicity against a normal cell line, renal proximal tubular epithelial cells (RPTEC).

Table 1 shows compounds that were tested for biological activity. These compounds are identified by an example number in the table, and are referred to herein by that Example or Compound number. In each case, for the compounds tested, the variable ring members in the left side were both nitrogen.

Table 2 shows results for $EC_{50}$ Hsp90α, $IC_{50}$ for Her2 degradation, and $IC_{50}$ for growth inhibition in SKBr3 breast cancer cells. All values in Table 2 in μM and represent an average of 3 measurements. As can be seen, the compositions tested all show substantial activity, and in many cases activity at nanomolar concentrations.

TABLE 1

| Example | $X_4$, $X_5$ | $X_2$ | linker | $X_3$ | X1 |
|---|---|---|---|---|---|
| 1 (PUH58) | —OCH$_2$O— | Br | S | H | pent-4-ynyl |
| 2 | Cl, Cl | Cl | S | H | pent-4-ynyl |
| 3 | 4-Cl, 5-methoxy | Cl | S | H | 2-isopropoxy-ethyl |
| 4 | Cl, Cl | Cl | S | H | H |
| 5 | —OCH$_2$O— | Br | S | H | N-isopropyl-n-propylamine |
| 6 (PUDZ2) | —OCH$_2$O— | Br | CH$_2$ | F | pent-4-ynyl |
| 7 (PUDZ3) | —OCH$_2$O— | Cl | CH$_2$ | F | pent-4-ynyl |
| 8 (PUDZ8) | —OCH$_2$O— | I | CH$_2$ | F | N-isopropyl-n-propylamine |
| 9 (PUH71) | —OCH$_2$O— | I | S | H | N-isopropyl-n-propylamine |
| 10 | —OCH$_2$O— | I | S | H | pent-4-ynyl |
| 11 | —OCH$_2$O— | I | CH$_2$ | F | pent-4-ynyl |
| 12 | 4,5-dimethoxy | I | CH$_2$ | F | pent-4-ynyl |
| 13 | 4,5-dimethoxy | Br | CH$_2$ | F | pent-4-ynyl |
| 14 | 4,5-dimethoxy | Cl | CH$_2$ | F | pent-4-ynyl |
| 15 | —OCH$_2$O— | I | CH$_2$ | H | N-isopropyl-n-propylamine |
| Comp 1 (PU24FCl) | 3',4',5'-trimethoxy | Cl | CH$_2$ | F | pent-4-ynyl |
| Comp 2 | 3',4',5'-trimethoxy | Cl | S | F | pent-4-ynyl |

TABLE 2

| Example | EC$_{50}$ Hsp90-α (μM) | IC$_{50}$ Her2 (μM) | IC$_{50}$ SKBr3 (μM) | Anti-mitotic |
|---|---|---|---|---|
| 1 | 0.03 ± 0.005 | 0.3 ± 0.05 | 0.2 ± 0.01 | Yes |
|   | .0508 ± .004 | 0.365 ± 0.0 45 | 0.300 ± 0.05 | Yes |
| 2 | 8.5 ± 0.1 | 58 ± 1.4 | 48.4 ± 2.5 | No |
| 3 | 5.0 ± 1.1 | 58.3 ± 2.2 | 16.1 ± 0.7 | No |
| 4 | 15.4 ± 2.2 | 47.8 ± 3.2 | 36.0 ± 0.2 | Yes |
| 5 | 0.0388 ± 0.003 | 0.205 ± 0.015 | 0.142 ± 0.022 | Yes |
| 6 | 0.0565 ± 0.002 | 0.210 ± 0.01 | 0.215 ± 0.055 | Yes |
| 7 | 0.0772 ± 0.001 | 0.300 ± 0.015 | 0.250 ± 0.030 | Yes |
| 8 | 0.0504 ± 0.004 | 0.080 ± 0.010 |  | Yes |
| 9 | 0.010.8 ± 0.002 | 0.100 ± 0.010 | 0.090 ± 0.002 | Yes |
| 11 | 0.0223 ± 0.002 | 0.090 ± 0.01 | 0.090 ± 0.03 | Yes |
| 12 | >15 | >50 | >50 | No |
| 13 | >15 | >50 | 55.0 ± 2.3 | No |
| 14 | 4.6 ± 0.02 | 30.0 ± 1.0 | 20.6 ± 6.7 | No |
| Comp 2 | 0.12 ± 0.3 | 1.3 ± 0.4 | 1.8 ± 0.2 | Yes |

Several active derivatives were tested for specificity towards transformed cells (Table 3). Binding affinities of selected compounds for average population Hsp90 complexes found in normal tissues (brain, lung and heart) and in addition, their cytotoxicities against RPTEC normal cells were determined. Compounds were found to bind Hsp90 from normal tissues with 2- to 3-log weaker affinities when compared to Hsp90 from SKBr3 cells. This specificity translated into 5 to 100-fold selectivity (column 10, Table 3) in inhibiting the growth of transformed cells compared to cultured normal epithelial cells (RPTEC tested). No cell death was observed in the purine-scaffold treated RPTEC cells even at the highest tested concentrations. Selectivity was also observed between SKBr3 cells and MRCS normal lung fibroblasts for compounds 9 and 10.

TABLE 3

| Ex. | EC$_{50}$ Hsp90 Brain | Ec$_{50}$ Hsp90 lung | EC$_{50}$ Hsp90 heart | EC$_{50}$ Hsp90 SKBr3 | Brain/ SKBr3 | Lung/ SKBr3 | Heart/ SKBr3 | IC$_{50}$ RPTEC | RPTEC/ SKBr3 |
|---|---|---|---|---|---|---|---|---|---|
| 1 | 40.2 ± 25.3 | 14.7 ± 1.7 | 65.3 ± 9.9 | 0.02 ± 0.06 | 2000 | 735 | 3265 | 4.1 ± 0.9 | 20.5 |
| 6 | ND | 5.20 ± 0.210 | 13.30 ± 0.210 | .0388 ± 0.003 | ND | 134 | 343 | ND | ND |
| 9 | ND | 2.40 ± 0.24 | 6.90 ± 0.15 | 0.0504 ± 0.004 | ND | 48 | 140 | ND | ND |
| 10 | ND | 2.20 ± 0.40 | 6.00 ± 0.20 | 0.0161 ± 0.001 | ND | 136 | 370 | ND | ND |
| Comp2 | 26.7 ± 7.7 | 217 ± 50 | 53.1 ± 20.5 | 0.09 ± 0.03 | 298 | 2400 | 590 | 28.1 ± 2.2 | 15.6 |

Figure 3B:
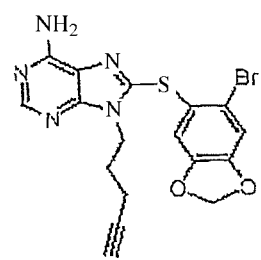
Figure 3C:
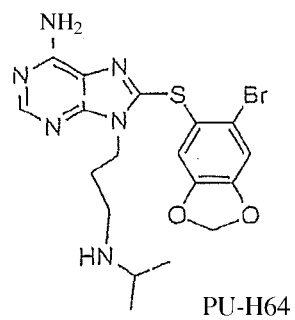
Figure 3D:
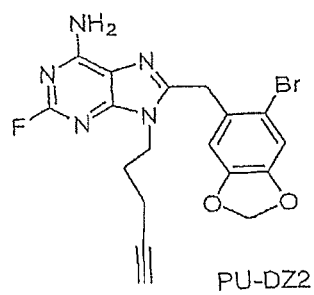
Figure 3E:
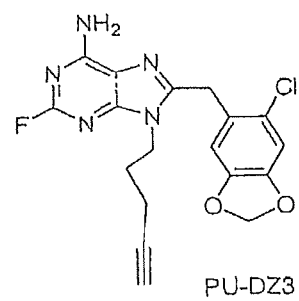
Figure 6B:
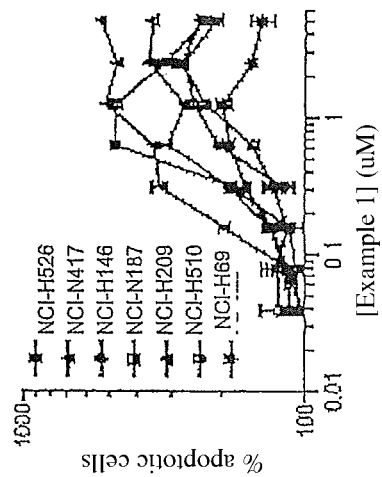
FIGS. 6A and B compare the effectiveness of PU24FC1 and a compound of the invention against various small cell lung cancer cells lines.
Figure 6A:
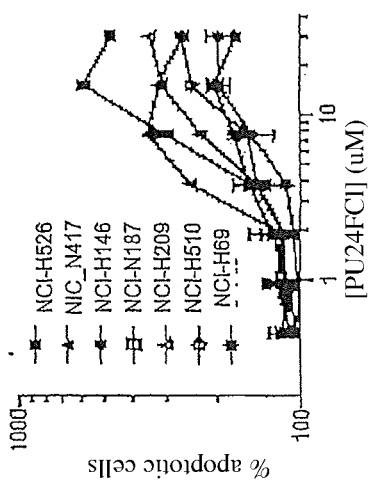

A compound in accordance with the invention having the structure shown in FIG. 3B (Compound 1) and PU24FC1, (Comparative 1, FIG. 1D) were tested for activity against 7 different small cell lung cancer cell lines (NCI-H69, NCI-H146, NCI-H209, NCI-H187, NCI-N417, NCI-H510 and NCI-H256) obtained from the American Type Culture Collection (Manassas, Va.). Both compounds exhibited binding to cellular Hsp90 as determined by homogenous fluorescence polarization. However, the concentration required of the compound of the invention was about 1 order of magnitude less than for PU24FC1. (Table 4) Antiproliferative effects of the two compounds were observed in the SCLC cell lines, and the percentage of apoptotic cells were determined. As shown in FIGS. 6A (PU24FC1) and B (Example 1), both compounds induced apoptosis in each of the SCLC cells lines, but the composition of the invention does so at a lower concentration. Both PU24FC1 and its higher potency derivative, Example 1, inhibit the growth and cause significant cytotoxicity against all SCLC cell lines. At concentrations of Hsp90 inhibitors in excess of 4-12 mM and 0.25-1 mM, respectively, 50-100% of the starting cell populations are dead at 72 h or 96 h post-treatment. As shown in Table 4 and FIGS. 6A and B, the 10 to 20-fold difference in binding for the two drugs correlate well with the their anti-proliferative potencies, suggesting that cell death in these cells is a direct result of Hsp90 inhibition.

TABLE 4

|  | IC$_{50}$ Comp 1 | IC$_{90}$ Comp 1 | EC$_{50}$ Comp 1 | IC$_{50}$ Examp 1 | IC$_{90}$ Examp 1 | EC$_{50}$ Exampl 1 | IC$_{50}$ Comp 1/Ex 1 | EC$_{50}$ Comp 1/Ex 1 |
|---|---|---|---|---|---|---|---|---|
| NCI-H526 | 4.2 ± 0.6 | 7.4 ± 0.1 | 0.229 ± 0.04 | 0.44 ± 0.04 | 0.83 ± 0.05 | 0.023 ± 0.02 | 9.5 | 9.6 |
| NCI-N417 | 3.5 ± 0.3 | 5.3 ± 0.4 | 0.592 ± 0.13 | 0.33 ± 0.03 | 0.61 ± 0.01 | 0.038 ± 0.01 | 10.6 | 15.4 |
| NCI-H146 | 5.8 ± 0.2 | 10.4 ± 0.2 | 0.574 ± 0.22 | 0.27 ± 0.04 | 0.49 ± 0.02 | 0.049 ± 0.02 | 21.5 | 13.1 |
| NCI-H187 | 6.5 ± 0.3 | 12.5 ± 0.5 | ND | 0.64 ± 0.02 | 1.2 ± 0.03 | ND | 8.3 | ND |
| NCI-H209 | 9.5 ± 0.5 | 11.6 ± 0.4 | 0.347 ± 0.06 | 0.50 ± 0.05 | 0.65 ± 0.04 | 0.021 ± 0.04 | 19.0 | 16.0 |
| NCI-H510 | 10.7 ± 0.1 | 13.4 ± 0.6 | ND | 0.76 ± 0.02 | 0.90 ± 0.09 | ND | 14.1 | ND |
| NCI-H69 | 2.5 ± 0.2 | 4.0 ± 0.1 | 0.350 ± 0.1 | 0.17 ± 0.02 | 0.25 ± 0.03 | 0.019 ± 0.01 | 14.7 | 17.8 |

Figure 7A:
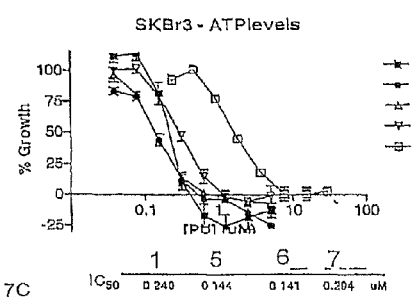
FIGS. 7A-D show experimental results for compounds in accordance with the invention, as compared to PU24FC1.

FIGS. 3B-E show the structure of four compounds (examples 1, 5, 6 and 7, respectively) in accordance with the invention made using the methods of Schemes 1 and 2. Where the 9N-alkyl chain is pent-4-ynyl, 5 and 10 were directly alkylated with using the Mitsonobu reaction and the corresponding alcohol. FIG. 7A-D shows test results for these compounds when compared to the prior art compound of FIG. 1D (Comp 1). FIG. 7A shows results when exponentially growing SKBr3 cancer cells were seeded into 96-well plates and incubated in medium containing either of vehicle control (DMSO) or the test compound (four replicate wells per assay condition) at the above indicated concentrations for 72 h at 37° C.

Figure 7B:
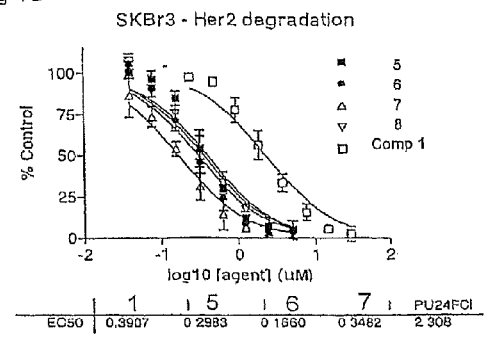
Figure 7C:
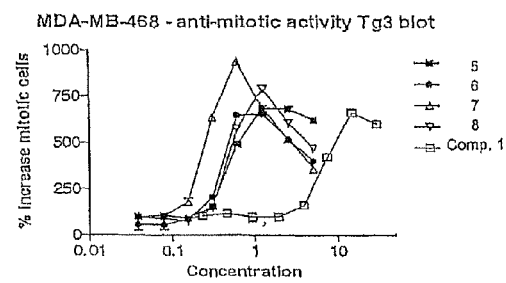
Figure 7D:
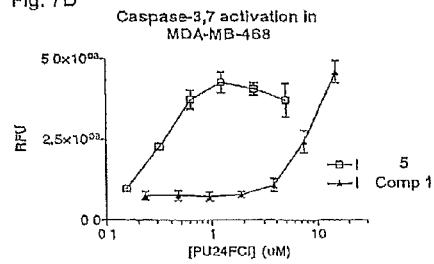

The antiproliferative effects of test compounds were evaluated using the CellTiter-Glo® Luminescent Cell Viability Assay kit from Promega Corporation. FIG. 7B shows results when exponentially growing SKBr3 cancer cells were seeded into 96-well plates and incubated in medium containing either of vehicle control (DMSO) or the test compounds (four replicate wells per assay condition) at the above indicated concentrations for 24 h at 37° C. The Her2 degradation potential of PUs was evaluated using our Her2 blot procedure described in PCT Patent Application Serial No. PCT/US04/21297, which is incorporated herein by reference. FIG. 7C shows results when exponentially growing MDA-MB-468 cancer cells were seeded into 96-well plates and incubated in medium containing either of vehicle control (DMSO) or the test compounds (four replicate wells per assay condition) at the above indicated concentrations for 24 h at 37° C. The anti-mitotic potential of compounds was evaluated using our Tg3 blot. The resulted chemiluminescent signal was read with an ANALYST® AD microplate reader. FIG. 7D shows the apoptotic inducing potential of PUs, which was assessed using caspase-3,7 activation as read-out. MDA-MB-468 cells (plated at 8,000/well) were plated in 96-well plates and treated for 24 h with varying concentration of compounds. For the caspase-3,7 assay, following treatment cells are lysed and permeabilized with our in-house developed buffer (10 mM HEPES pH. 7.5, 2 mM EDTA, 0.1% CHAPS, 0.1 mg/ml PMSF, COMPLETE™ Protease Inhibitor Mix, Roche) to make them accessible to the caspase-3,7 substrate Z-DEVD-R110. This agent becomes highly fluorescent upon cleavage by activated caspase-3,7 and subsequent release of rhodamine, thus the assay is a simple read-mix procedure. The resulted fluorescence signal will be read using the SPECTRAMAX® Gemini XS (Molecular Devices) (ex. 485, em. 530). As is apparent from these figures, the four compositions of the invention all produced similar results to one another, but were active at significantly lower concentrations than the comparison compound.

Figure 8:
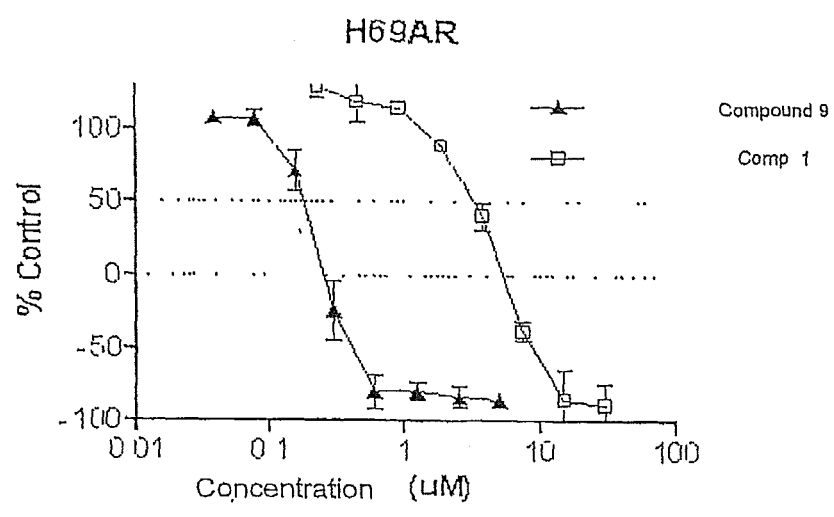
FIG. 8 shows inhibition of cell growth and induction of cell death in SCLC cells highly resistant to conventional chemotherapy using Example 9 in accordance with the invention.
Figure 9A:
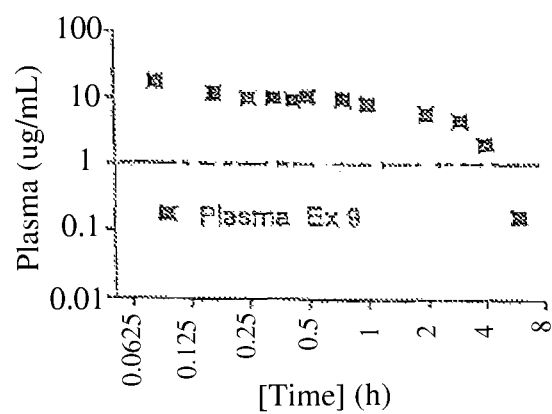
FIGS. 9A-D show a comparison of Example 9 in accordance with the invention and prior art compounds for efficacy against small cell lung tumors.
Figure 9B:
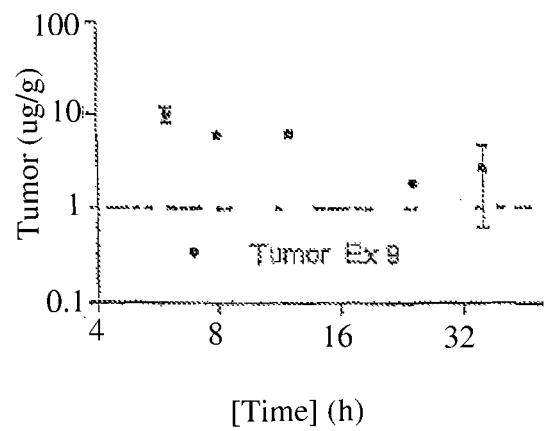
Figure 9C:
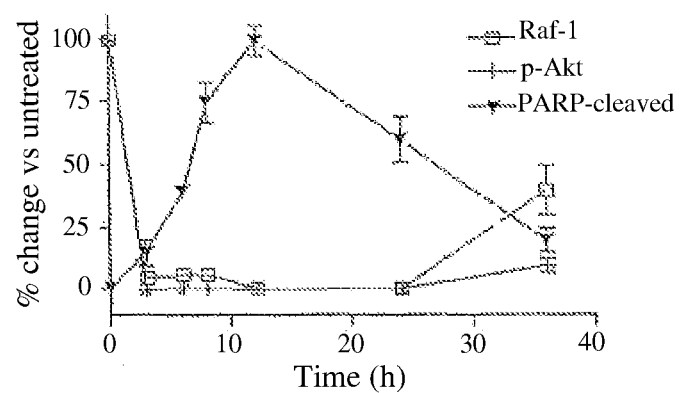
Figure 9D:
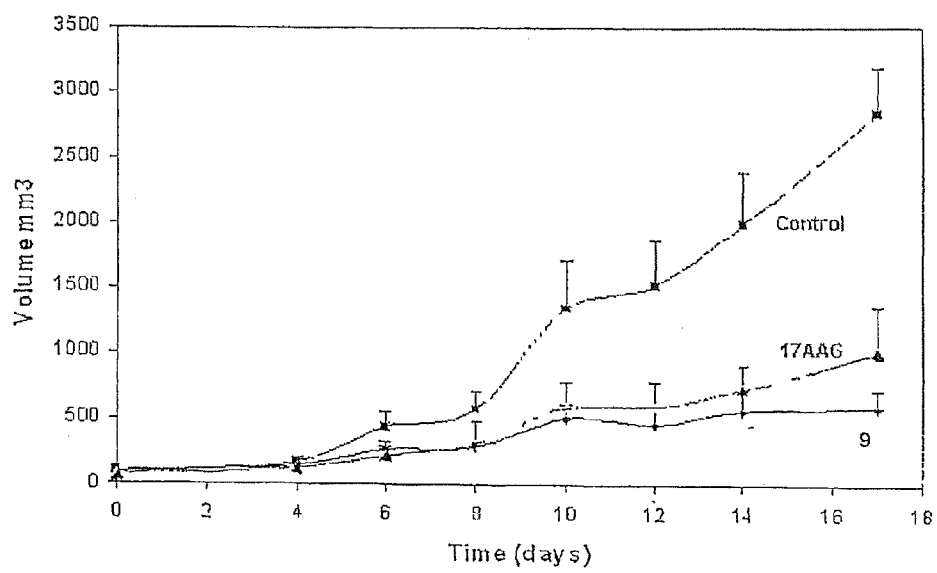

The compounds of FIGS. 3F and 3G (Examples 8 and 9) are water soluble when in the acid addition salt form (solubility>5 mM in PBS) and have low nanomolar potency against cancer cells. The pharmacokinetic and pharmacodymanic profiles, as well as the anti-cancer activity of Compound 9 were tested in a model of small cell lung cancer. Small cell lung carcinoma (SCLC) is a highly malignant tumor accounting for about 20% of all lung cancers. It is a disease that metastasises early and widely, accounting for the extremely poor prognosis of this tumor. Whereas it often initially responds well to chemotherapy, relapses occur almost without exception, and they are usually resistant to cytotoxic treatment. We have shown that compound of FIG. 3G (Example 9) retains its activity in H69AR, a SCLC cell line resistant to adriamycin as well as in SKI-Chen, a cell line derived at MSKCC from a patient who failed to respond to every conventional therapy. The H69AR line was established from NCI-H69 cells that were grown in the presence of increasing concentrations of adriamycin (doxorubicin) over a total of 14 months. The cell line is cross-resistant to anthracycline analogues including daunomycin, epirubicin, menogaril, and mitoxantrone as well as to acivicin, etoposide, gramicidin D, colchicine, and the Vinca alkaloids, vincristine and vinblastine, and expresses the multidrug resistance protein. Growth over 96 h was assessed. FIG. 8 shows a comparison of results for Compound 9 and PU24FC1. Values below 0% represent cell death of the starting population. As shown, the compound of the invention is effective at a concentration about 20 times lower.

Figure 1D:
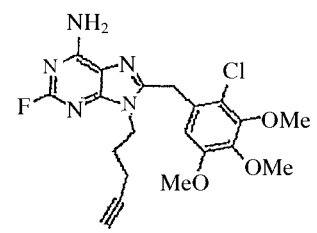
Figure 2:
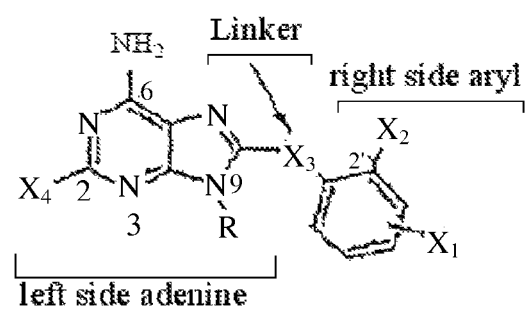
FIG. 2 shows a general structure of embodiments of a purine-scaffold Hsp90 inhibitor in accordance with the invention in which the left side is an adenine (N at 1 and 3 positions).

In vivo, Example 9 exhibits the tumor retention profile manifested by our early micromolar compound of FIG. 1D (Comp 1) as shown in FIGS. 9 A and B. While Example 9 is rapidly cleared from plasma, with levels undetectable after 6 h post-administration, it is retained in tumors at pharmacologic doses for more than 36 h. Such behavior translates in considerable downregulation for more than 36 h of Hsp90 client proteins driving transformation in this tumor. Proteins involved in growth and survival potential of the tumor, Raf-1 and Akt, are efficiently degraded or inactivated (pAkt) by one administered dose of Example 9. In addition, the agent induces significant apoptosis of the tumor as reflected by an increase in PARP cleavage. (FIG. 9C) This is the first indication of apoptosis induced in vivo by an Hsp90 inhibitor. Concordantly, Example 9 efficiently inhibited the growth of this tumor in a manner comparable to 17AAG without toxicity to the host (FIG. 9D).

Figure 10:
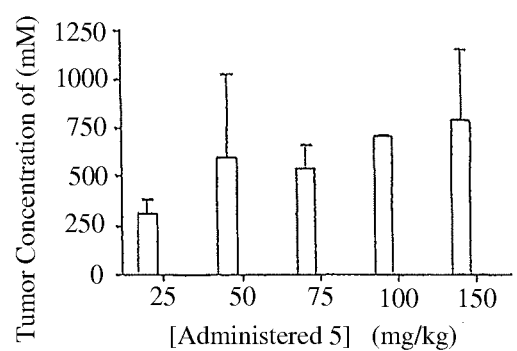
FIGS. 10A and B show pharmacodynamic effects of Compound 6 when administered to MDA-MB bearing mice.

Mice xenografted with MDA-MB-468 human breast cancer tumors were treated by intraperitoneal injection with Compound 5 at a dosage levels of 25, 50, 75, 100 and 150 mg/kg. The concentration of Compound 5 in the tumor 24 hours after administration was determined. As reflected in FIG. 10A, at all dosage levels a biologically active concentration of 300 nM was observed in the tumor, although it could not be detected in plasma. Compound 5 was further tested for its effects on the pharmacodynamic marker Raf-1 kinase.

Figure 10B:
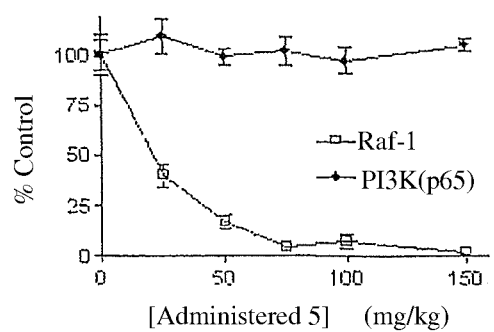

Hsp90 stabilizes this kinase and maintains it in ready-to-be-activated conformation. Inhibition of Hsp90 leads to disruption of the complex and further ubiquitinylation and degradation of Raf-1 by the proteasome. Thus, Raf-1 degradation in tumors is a functional read-out of Hsp90 inhibition. FIG. 10B shows % control levels of Raf-1 protein in mice to which Compound 5 was administered. As shown, substantial decrease in Raf-1 levels was observed at all dosage levels. In contrast, no change in expression of PD kinase, a protein unaffected by Hsp90 inhibitors.

Observation of Selective Activity

Although the change of the linker structure between $CH_2$ and S did not result in significant change in activity measured in the biological assays described above, this work has allowed the identification of Hsp90 inhibitors that demonstrate selective affinities for certain Hsp90-client protein complexes. Compounds Example 1 and Comp 2 induced Her2 degradation and inhibition of growth in SKBr3 cells, and also exhibited anti-mitotic activity in MDA-MB-468 cells, these events occurring with similar potencies. However, among the moderate affinity binders, derivatives were identified that degrade Her2 with corresponding potencies but do not affect cell cycle distribution in RB-defective cells at similar concentrations. The Hsp90 client protein of whose inactivation by Hsp90 inhibitors is responsible for the block of these cells in mitosis is currently unknown. Due to their selectivity profile, these derivatives may be useful pharmacological tools in dissecting Hsp90-regulated processes.

A study comparing the activity of pairs of compounds differing only in the nature of the linker indicated that in general, compounds with $CH_2$ as the linker are antimitotic, while compounds with S as the linker are not. Consistent with this observation, caspase 3,7 assays showed that compounds with a $CH_2$ linker induce apoptosis in Rb defective cells, while the S compound does not, This is indicative of a selective affinity to hsp90 complexes in these cells. Both S and $CH_2$ compounds may have comparable affinity for hsp90 complexes that regulate cell growth and survival, regardless of Rb-type, while the S compounds are more weakly bound to hsp90 complexes that regulate transition through mitosis in Rb-defective cells. As a result of this selectivity, S compounds are more beneficial in the treatment of diseases/conditions where apoptotis is not desired. This would include neurodegenerative diseases, ischemia, inflammation, HIV and nerve regeneration.

Compositions Coupled to Targeting/Labeling Moieties

The compounds of the invention may be coupled via N9 to a targeting moiety selected to specifically bind to a protein, receptor or marker found on a target population of cells. The targeting moiety may be a hormone, hormone analog, protein receptor- or marker-specific antibody or any other ligand that specifically binds to a target of interest, and is selected on the basis of the identity of the target. Particular targeting moieties bind to steroid receptors, including estrogen and androgen and progesterone receptors, and transmembrane tyrosine kinases, src-related tyrosine kinases, raf kinases and PI-3 kinases. Specific tyrosine kinases include HER-2 receptors and other members of the epidermal growth factor (EGF) receptor family, and insulin and insulin-like growth factor receptors. Examples of specific targeting moieties include estrogen, estradiol, progestin, testosterone, tamoxifen and wortmannin. Targeting moieties may also be antibodies which bind specifically to receptors, for example antibodies which bind to Her2 receptors as disclosed in International Patent Publications Nos. WO96/32480, WO96/40789 and WO97/04801, which are incorporated herein by reference.

Figure 4:
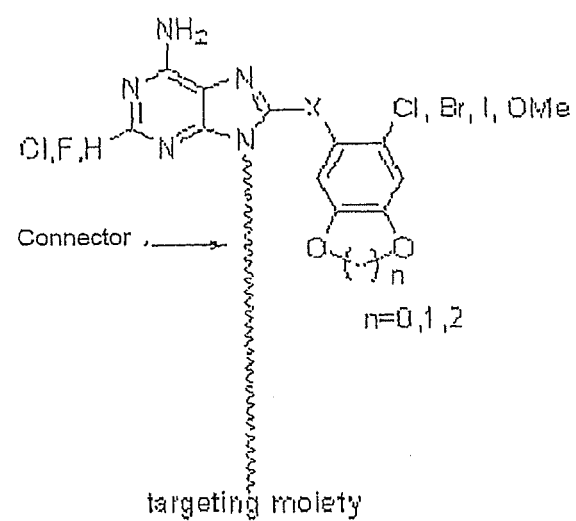
FIG. 4 shows the structure of an exemplary Hsp90 inhibitor connected to a targeting moiety via a connector.

FIG. 4 shows an exemplary structure of a composition of the invention that includes a targeting moiety connected to the nitrogen at the 9 position of the purine via a connector. The linker may be any generally linear chain which is of sufficient length permit the targeting moiety and the purine scaffold molecule to interact with their particular targets when associated together, or may be a linker adapted for controlled cleavage once targeting has been accomplished. The linker may be a $C_4$ to $C_{20}$ hydrocarbon chain, or may include intermediate heteroatoms such as O or N. Commonly, the linker is coupled to N-9 of the purine scaffold using the same synthetic mechanisms for adding substituents to the N-9 position. Terminal functional groups, such as amino or carboxyl groups, on the linker are used to form a bond with reactive sites on the selected targeting moiety.

In lieu of a targeting moiety, the compounds of the invention may include a labeling moiety attached via a connector to the N9 position. Examples of labeling moieties include without limitation biotin. As in the case of a targeting moiety, the connector is not critical in structure, and need only be of sufficient length so that the labeling moiety does not interfere with the interaction of the purine scaffold portion of the molecule with Hsp90.

Use of the Compositions of the Inventions

Because of their ability to bring about the degradation of proteins which are essential to cellular function, and hence to retard growth and/or promote cell death, the hsp90-binding compounds of the invention, with or without a targeting moiety, can be used in the therapeutic treatment of a variety of disease conditions. A suitable therapeutic is one which degrades a kinase or protein that is found in enhanced amounts or is mutated in disease-associated cells, or on which the viability of such cells depends. The general role of HSP90 proteins in maintaining malignancy in most cancer cells points to the importance of this target in the development of anticancer agents. Thus, the therapeutic small molecules of the invention provide a novel modality for the treatment of all cancers that require or are facilitated by an HSP90 protein. For example, the compositions of the invention can be used in the treatment of a variety of forms of cancer, particularly those that overexpress Her2 or mutated or wild type steroid receptors, or that lack functional RB protein. Such cancers may include but are not limited to breast cancer, small cell lung cancer, amyelocytic leukemia, vulvar cancer, non-small cell lung cancer, colon cancer, neuroblastoma and prostate cancer. In addition, the compositions of the invention can be used in the treatment of other diseases by targeting proteins associated with pathogenesis for selective degradation. Examples of such targetable proteins include antigens associated with autoimmune diseases and pathogenic proteins associated with Alzheimer's disease.

The compositions of the invention exhibit the ability to degrade specific kinases and signaling proteins. Furthermore, selectivity for transformed versus normal cells can be observed, as reflected in Table 3. For example, compound example 1 (FIG. 3B) shows very high selectivity for tumor cells as opposed to normal heart, brain or lung tissue. The precise mechanism for this selectivity is not known, although it is believed to arise from a higher affinity for tumor hsp90 as opposed to normal cells hsp90.

The compositions of the invention are administered to subjects, including human patients, in need of treatment, in an amount effective to bring about the desired therapeutic result. A suitable administration route is intravenous administration, which is now commonly employed in chemotherapy. In addition, because the compositions of the inventions are small soluble molecules, they are suitable for oral administration. The ability to use an oral route of administration is particularly desirable where it may be necessary to provide treatment of a frequent, for example a daily schedule. The amount of any given composition to be administered, and the appropriate schedule for administration are determined using toxicity tests and clinical trials of standard design, and will represent the conclusion drawn from a risk benefit analysis. Such analyses are routinely performed by persons skilled in the art, and do not involve undue experimentation.

Due to the higher affinity these agents manifest towards cancer cells and their preferential tumor retention profile, these agents are useful as tumor imaging agents. They may also be used to monitor the response of tumors to Hsp90-targeted therapy. The compounds of FIGS. 3F and G (Examples 8 and 9) were iodinated with $^{131}I$ using chloramine T and tributyltin precursors. The radioligands were purified by Cl 8 RP HPLC. The saturation binding of these agents to CWR22-rv1 prostate cancer cells was undertaken. Animal biodistribution studies and MicroPET imaging were also performed in nude mice with CWR22 transplantable tumors using $^{124}I$-labeled compounds. These studies showed the uptake of the radiolabeled compounds, and the ability to use these compounds in radioimaging to provide an image of a tumor.

Other options for radiolabeling include $^{18}F$ which can be used in positron emission tomography (PET). $^{123}I$-labeled compounds can be used in single photon emission computed tomography (SPECT), and $^{125}I$-labeled compounds can be used in surgical gamma probe detection.

The compositions of the invention also have utility to enhance the sensitivity of tumors to other forms of therapy, such as radiation and chemotherapy. This utility can be applied in the context of any type of tumor, but it is particularly relevant in the treatment of gliomas. Given the current therapeutic challenge due to radioresistance and chemoresistance explaining the poor prognosis (median survival of 12 months) in GBM, identification of agents that may both sensitize gliomas to radiation and further act as treatments in inhibiting the growth of these tumors is necessary. Multipathway-targeted therapy using single agents that target multiple pathways, including HDAC and Hsp90 inhibitors hold promise for improved radiation therapy efficacy and, ultimately, improved patient outcome. Because radiotherapy remains a primary treatment modality for gliomas, the ability to enhance glioma cell radiosensitivity should provide a therapeutic advantage. Previous studies using 17 AAG and 17DMAG have suggested that Hsp90 is a clinically relevant target for the radiosensitization of a wide variety of tumors (Russell et al, Clinical Cancer Research 9: 3749-3755, 2003; Bull et al, Clinical Cancer Research 10: 8077-8084, 2004). However, whereas in vitro studies have indicated that these Hsp90 inhibitors enhance glioma cell radiosensitivity, 17AAG and 17DMAG do not penetrate the blood brain barrier and thus do not appear applicable to brain tumor therapy.

Compound 9 has been shown to have the ability to cross the blood brain barrier and therefore is suitable for combination with radiotherapy as a novel form of brain tumor treatment. Initial studies based on the clonogenic survival assay indicate that Compound 9 enhances the in vitro radiosensitivity of two human glioma cell lines (U251 and U87) with dose enhancement factors of 1.4-1.6, a degree of radiosensitization similar to that previously shown for 17AAG and 17DMAG. Cells were exposed to 200 nM or 400 nM Compound 8 or 9 for 16 h, irradiated with graded doses of X rays, rinsed and fed with fresh growth media. Colony forming efficiency was determined 10-12 days later and survival curves generated after normalizing for cell killing by Compound 9 alone. The results are summarized in Fig 11A (Compound 9) and B (Compound 8).

The surviving fractions after Compound 9 treatment only were 0.86 and 0.68 for U251 and U87 cells, respectively.

The following procedures and experiments were performed, and are provided here to further demonstrate the invention.

Hsp90 competition assay. Fluorescence polarization measurements were performed on an ANALYST® AD instrument (Molecular Devices, Sunnyvale, Calif.). Measurements were taken in black 96-well microtiter plates (Corning #3650). The assay buffer (HFB) contained 20 mM HEPES (K) pH 7.3, 50 mM KCl, 5 mM $MgCl_2$, 20 mM $Na_2MoO_4$, 0.01% NP40. Before each use, 0.1 mg/mL bovine gamma globulin (BGG) (Panvera Corporation, Madison, Wis.) and 2 mM DTT (Fisher Biotech, Fair Lawn, N.J.) were freshly added. GM-BODIPY was synthesized as previously reported[23a] and was dissolved in DMSO to form 10 μM solutions. Recombinant Hsp90α was purchased from Stressgen Bioreagents (cat. No. SPP-776), (Victoria, Canada). Cell lysates were prepared rupturing cellular membranes by freezing at −70° C. and dissolving the cellular extract in HFB with added protease and phosphotase inhibitors. Organs were harvested from a healthy mouse and homogenized in HFB. Saturation curves were recorded in which GM-BODIPY (5 nM) was treated with increasing amounts of cellular lysates. The amount of lysate that resulted in polarization (mP) readings corresponding to 20 nM recombinant Hsp90α was chosen for the competition study. For the competition studies, each 96-well contained 5 nM fluorescent GM, cellular lysate (amounts as determined above and normalized to total Hsp90 as determined by Western blot analysis using as standard Hsp90 purified from HeLa cells (Stressgen#SPP-770) and tested inhibitor (initial stock in DMSO) in a final volume of 100 μL. The plate was left on a shaker at 4° C. for 7 h and the FP values in mP were recorded. $EC_{50}$ values were determined as the competitor concentrations at which 50% of the fluorescent GM was displaced.

Cell culture. The human breast cancer cell lines SKBr3 and MDA-MB-468 were a gift from Dr. Neal Rosen (MSKCC). Cells were maintained in 1:1 mixture of DME:F12 supplemented with 2 mM glutamine, 50 units/mL penicillin, 50 units/mL streptomycin and 10% heat inactivated fetal bovine serum (Gemini Bioproducts#100-10b) and incubated at 37° C., 5% $CO_2$. Growth assays. Growth inhibition studies were performed using the sulforhodamine B assay as previously described.[29] In summary, experimental cultures were plated in microtiter plates (Nunc#167008). One column of wells was left without cells to serve as the blank control. Cells were allowed to attach overnight. The following day, growth medium having either drug or DMSO at twice the desired initial concentration was added to the plate in triplicate and was serially diluted at a 1:1 ratio in the microtiter plate. After 72 h of growth, the cell number in treated versus control wells was estimated after treatment with 50% trichloroacetic acid and staining with 0.4% sulforhodamine B in 1% acetic acid. The $IC_{50}$ was calculated as the drug concentration that inhibits cell growth by 50% compared with control growth. Normal human renal proximal tubular epithelial (RPTEC) cells were purchased pre-seeded in 96-well plates (Clonetics, CC-3190). Upon receipt, cells were placed in a humidified incubator at 37° C., 5% $CO_2$ and allowed to equilibrate for 3 h. Media was removed by suction and replaced with fresh media provided by the manufacturer. Cells were then treated with either drugs or DMSO for 72 h and the $IC_{50}$ values were determined as described above.

Her2 assay. SKBr3 cells were plated in black, clear-bottom microtiter plates (Corning#3603) at 3,000 cells/well in growth medium (100 μl) and allowed to attach for 24 h at 37° C. and 5% CO2. Growth medium (100 μl) with drug or vehicle (DMSO) was carefully added to the wells, and the plates were placed at 37° C. and 5% $CO_2$. Following 24 h incubation with drugs, wells were washed with ice-cold Tris buffer saline (TBS) containing 0.1% Tween 20 (TBST) (200 μl). A house vacuum source attached to an eight-channel aspirator was used to remove the liquid from the plates. Further, methanol (100 μl at −20° C.) was added to each well, and the plate was placed at 4° C. for 10 min. Methanol was removed by washing with TBST (2×200 μl). After further incubation at RT for 2 h with SUPERBLOCK® R (Pierce 37535) (200 μl), anti-Her-2 (c-erbB-2) antibody (Zymed Laboratories#28-004) (100 μl, 1:200 in SUPERBLOCK® R) was placed in each well. The plate was incubated overnight at 4° C. For control wells, 1:200 dilution of a normal rabbit IgG (Santa Cruz#SC-2027) in SUPERBLOCK® R was used. Each well was washed with TBST (2×200 μl) and incubated at RT for 2 h with an anti-rabbit HRP-linked antibody (Sigma, A-0545) (100 μl, 1:2000 in SuperBlockR). Unreacted antibody was removed by washing with TBST (3×200 μl), and the ECL™ Western blotting reagent (Amersham #RPN2106) (100 μL) was added. The plate was immediately read in an Analyst AD plate reader (Molecular Devices). Each well was scanned for 0.1 s. Readings from wells containing only control IgG and the corresponding HRP-linked secondary antibody were set as background and deducted from all measured values.

Luminescence readings resulted from drug-treated cells versus untreated cells (vehicle treated) were quantified and plotted against drug concentration to give the $EC_{50}$ values as the concentration of drug that caused 50% decrease in luminescence.

Anti-mitotic assay. Black, clear-bottom microtiter 96-well plates (Corning Costar#3603) were used to accommodate experimental cultures. MDA-MB-468 cells were seeded in each well at 8,000 cells per well in growth medium (100 μL), and allowed to attach overnight at 37° C. and 5% $CO_2$. Growth medium (100 μL) with drug or vehicle (DMSO) was gently added to the wells, and the plates were incubated at 37° C. and 5% $CO_2$ for 24 h. Wells were washed with ice-cold TBST (2×200 μL). A house vacuum source attached to an eight-channel aspirator was used to remove the liquid from the 96-well plates. Ice-cold methanol (100 μL) was added to each well, and the plate was placed at 4° C. for 5 min. Methanol was removed by suction and plates were washed with ice-cold TBST (2×200 μL). Plates were further incubated with SuperBlock® blocking buffer (Pierce #37535) (200 μL) for 2 h at RT. The Tg-3 antibody (gift of Dr. Davies, Albert Einstein College of Medicine) diluted 1:200 in SuperBlock® was placed in each well (100 μL) except the control column that was treated with control antibody (Mouse IgM, NeoMarkers, NC-1030-P). After 72 h, wells were washed with ice-cold TBST (2×200 μL). The secondary antibody (Goat Anti-Mouse IgM, SouthernBiotech #1020-05) was placed in each well at 1:2000 dilution in SuperBlock®, and incubated on a shaker at RT for 2 h. Un-reacted antibody was removed by washing the plates with ice-cold TBST (3×200 μL) for 5 min on a shaker. The ECL™ Western Blotting Detection Reagents 1 and 2 in 1:1 mix (100 μL) was placed in each well and the plates were read immediately in an Analyst AD plate reader (Molecular Devices). Luminescence readings were imported into SOFTmax PROR 4.3.1. Anti-mitotic activity was defined as a concentration dependent increase in luminescence readings in compound-treated wells as compared to DMSO only treated wells.

General Chemical Procedures. AU commercial chemicals and solvents are reagent grade and were used without further purification. The identity and purity of each product was characterized by MS, HPLC, TLC, IR and NMR. $^1$H NMR/$^{13}$C NMR spectra were recorded on a Bruker 400 MHz instrument. Low-resolution mass spectra (MS) were recorded in the positive ion mode under electron-spray ionization (ESI). High performance liquid chromatography analyses were performed on a Waters 2996 instrument with a photodiode array detector (read at 265 nm) and a reverse-phase column (Higgins; HAISIL HL C18 5 μm) (method (a)) and additionally, a Waters 2695 Separation Module with a Waters 996 photodiode array detector and a Waters micromass ZQ and a reverse-phase column (Varian; Microsorb 100-5 C18 150×2) (methods (b) and (c)). Method (a): 0.1% TFA in water-acetonitrile in the indicated ratio; method (b): 0.05% TFA in water-0.04% TFA in acetonitrile; method (c): 0.05% TFA in water-0.04% TFA in acetonitrile gradient (35% acetonitrile over 18 min, 35-95% acetonitrile over 6 min, 95% acetonitrile over 9 min). Infrared spectra (IR) were obtained on a Perkin-Elmer FT-IR model 1600 spectrometer. Characterization data for previously unknown compounds were determined from a single run with isolated yields. Reactions were monitored by thin-layer chromatography on 0.25-mm silica gel plates and visualized with UV light. Column chromatography was performed using silica gel (Fisher 170-400 mesh) or alumina (Fisher 60-325 mesh). Oxidation reactions with OXONE® were carried out in the presence of the Fisher alumina (A540; 80-200 mesh). Analytical thin-layer chromatography (TLC) was performed on E. Merck precoated silica gel 60 F254. Waters Sep-PakR Vac 6 cc (500 mg) Cl 8 cartridges were used for the purification of compounds 16. All reactions were conducted under inert atmosphere except of those in aqueous media.

3,4,5-Trimethoxy-benzenethiol (6). To 3,4,5-trimethoxyaniline (2 g, 10.9 mmol) at 0° C. were added a concentrated solution of HCl (3 mL, 0.27 mL/mmol) and $H_2O$ (7.7 mL) followed by $NaNO_2$ (932 mg, 13.1 mmol). The resulting solution was poured over potassium ethyl xanthogenate (5.35 g, 32.7 mmol) in H2O (6.2 mL) and stirred at 50° C. for 40 min. The reaction mixture was brought to room temperature, diluted with EtOAc (80 mL) and washed with 10% NaOH, followed by $H_2O$ until the pH reached 7. The organic fraction was dried over $Na_2SO_4$ and the solvent evaporated under high vacuum. The residue was purified by column chromatography on silica gel ($CH_2Cl_2$) to furnish the xanthogenate intermediate (1.82 g, 58% yield). This was taken up in anhydrous THF (30 mL). To the resulting solution, $LiAlH_4$ (I g, 25 mmol) was slowly added and the mixture was stirred for 1 h at reflux temperature. Following cooling to room temperature, the reaction was quenched with ice cold water (50 mL) and 10% $H_2SO_4$ (5 mL) and extracted with $CHCl_3$. The organic phase was dried over $Na_2SO_4$ and evaporated to give the desired thiophenol (1.18 g, 93% yield). $^1$H NMR ($CDCl_3$) δ6.53 (s, 2H), 3.84 (s, 6H, OCH3), 3.82 (s, 3H, OCH3), 3.46 (s, $^1$H, SH).

Procedures for the formation of 8-arylsulfanyladenine derivatives: Scheme 1, synthetic step (b). 8-Mercaptoadenine (7) (50.2 mg, 0.30 mmol), neocuproine hydrate (6.8 mg, 0.03 mmol), CuI (5.7 mg, 0.03 mmol), NaO-t-Bu (57.6 mg, 0.6 mmol), the corresponding aryl iodide (0.90 mmol) and anhydrous DMF (2 mL) were charged in a nitrogen box. The reaction vessels were sealed with Teflon tape, placed in an oil bath (110° C.) and magnetically stirred for 24 h. The reaction mixture was then cooled to room temperature and DMF was removed in vacuo. The crude was purified by silica gel flash chromatography eluting with a gradient of $CHCl_3$:$NH_4OH$ at 10:0.5 to $CHCl_3$:MeOH:$NH_4OH$ at 10:1:0.5 to afford the desired product.

8-(2,4,5-Trichloro-phenylsulfanyl)adenine. Use $K_2CO_3$ as base. Yield, 56%. $^1$H NMR (400 MHz, DMSO-d6) δ8.12 (s, 1H), 8.00 (s, 1H), 7.60 (s, 1H), 7.37 (s, 2H); $^{13}$C NMR (100 MHz, DMSO-d6) δ132.5, 132.3, 132.2, 131.4, 131.2, 130.8; MS m/z 345.9 (M+H)+. HPLC: (a) 99.9% (65% water-35% acetonitrile); (b) 99.4%.

Scheme 1, synthetic step (d): A mixture of 8-arylsulfanyl adenine 10 (100 μmol), Cs2CO3 (100 μmol), pent-4-ynyl 4-methylbenzenesulfonate (120 μmol) in DMF (1.3 mL) under nitrogen protection was heated at 80° C. for 30 min Following solvent removal, the crude was purified by preparatory TLC with $CHCl_3$:MeOH:NH4OH at 10:1:0.5 or $CHCl_3$:MeOH: AcOH at 10:1:0.5 to provide the corresponding 9-alkyl-8-arylsulfanyladenine derivatives 11.

9-(Pent-4-ynyl)-8-(2,4,5-trichloro-phenyIsulfanyI)adenine (Hu). Yield, 46%. $^1$H NMR (400 MHz, CDC13/MeOD-d4) δ8.26 (s, 1H), 7.63 (s, 1H), 7.50 (s, 1H), 4.38-4.35 (t, J=7.3 Hz, 2H), 2.32-2.28 (m, 2H), 2.09-2.02 (m, 3H); $^{13}$C NMR (100 MHz, CDC13/MeOD-d4) δ154.4, 152.7, 150.9, 143.8, 134.1, 133.7, 133.4, 131.9, 131.3, 129.4, 81.8, 69.4, 42.9, 28.1, 15.7; MS m/z 411.9 (M+H)+. HPLC: (a) 98.5% (75% water-25% acetonitrile); (b) 97.1%.

9-(Pent-4-ynyl)-8-(6-bromo-benzo[1,3]dioxol-5-ylsulfanyl)adenine. Yield, 48%. $^1$H NMR (400 MHz, CDC13/MeOD-d4) δ8.22 (s, 1H), 7.17 (s, 1H), 7.00 (s, 1H), 6.06 (s, 2H), 4.35-4.31 (t, J=7.26 Hz, 2H), 4.12 (s, 2H), 2.33-2.30 (m, 2H), 2.08-2.05 (m, 3H). $^{13}$C NMR (100 MHz, CDC13/

MeODd4) δ150.9, 149.7, 148.0, 146.9, 121.3, 119.1, 113.8, 113.4, 102.4, 81.9, 69.3, 42.7, 28.0, 15.6; MS m/z 432.0 (M+H)+. HPLC: (a) 98.7% (75% water-25% acetonitrile); (b) 98.9%.

9-(2-Isopropoxy-ethyl)-8-(2,4-dichloro-5-methoxy-benzenesulfanyl)adenine. Following the general method for the preparation of 12d, IIe3 afforded 12c. Yield, 53%. $^1$H NMR (400 MHz, CDC13) δ8.36 (s, 1H, H-2), 7.44 (s, 1H), 7.09 (s, 1H), 5.55 (bs, 2H, NH2), 4.48 (t, J=5.6 Hz, 2H, NCH2), 3.81 (s, 3H, OCH3), 3.74 (t, J=5.6 Hz, 2H), 3.49 (d, J=6.1 Hz, $^1$H, CH), 1.04 (d, J=6.1 Hz, 6H, CH3); 13C NMR (100 MHz, CDC13) δ154.1 (C-2), 153, 147, 131.0, 130.2, 126.9, 123.6, 116.0, 72.3 (CH), 65.6, 56.5 (OCH3), 44.1 (NCH2), 21.8 (CH2); MS (EIS) m/z 428.0 (M+1)+. HPLC: (a) 90.2% (70% water-30% acetonitrile); (c) 91.0%.

Method for the fluorination of the adenine moiety at C2: 2-Fluoro-9-butyl-8-(2-chloro-3,4,5-trimethoxy-phenylsulfanyl)adenine (21c). To a cooled solution (0° C.) of 18c (11.3 mg, 0.02 mmol) in HF/pyridine (18 μL, 0.7 mL/mmol) NaNO2 (2.2 mg, 0.03 mmol) was slowly added. The resulting mixture was stirred at room temperature for 1 h and then quenched by stirring for 1 h with 14 mg of CaCCβ in CH2C12 (75 μL). The crude was taken up in CH2C12, washed with water and dried over anhydrous Na2SO4. Following solvent removal, the residue was purified on a preparative silica gel plate (CHC13:Hexanes:EtOAc:i-PrOH at 2:2:1:0.1) to afford 21c (1.9 mg, 17% yield). IR (film) $v_{max}$ 3318-2953, 1657, 1604, 1583, 1479, 1385, 1111, 1015; $^1$H NMR (400 MHz, CDC13) δ6.72 (s, 1H), 5.83 (bs, 2H, NH2), 4.18 (t, J=7.5 Hz, 2H, NCH2), 3.92 (s, 3H, OCH3), 3.89 (s, 3H, CH3), 3.74 (s, 3H, CH3), 1.72 (m, 2H), 1.32 (m, 2H), 0.92 (t, J=7.4 Hz, 3H, CH3); $^{13}$C NMR (100 MHz, CDC13) δ160.1, 158.0, 156.1, 152.5, 150.8, 143.9, 124.6, 111.2, 61.2 and 56.3 (OCH3), 43.9 (NCH2), 31.7, 29.7, 19.7 (CH3); MS (EIS) m/z 442.2 (M+1)+. HPLC: (a) 95.9% (60% water-40% acetonitrile); (c) 98.0%.

8-(6-Bromo-benzo[1,3]dioxol-5-ylsulfanyl)adenine. 8-Mercaptoadenine (602 mg, 3.6 mmol), neocuproine hydrate (81 mg, 0.36 mmol), CuI (69 mg, 0.36 mmol), NaO-t-Bu (692 mg, 7.2 mmol), 5-bromo-6-iodo~benzo[1,3]dioxole (3.53 g, 10.8 mmol) and anhydrous DMF (24 mL) were charged in a nitrogen box. The vessel was sealed with Teflon tape, placed in an oil bath (110° C.) and magnetically stirred for 24 h. The solvent was removed under high vacuum and the crude purified by column chromatography on silica gel (EtOAc:CH2C12:MeOH at 2:2:1) to provide the product (1.29 g, 97%). $^1$H NMR (400 MHz, acetone-d6) 8.07 (s, 1H), 7.28 (s, 1H), 7.15 (s, 1H), 7.08 (bs, 1H), 6.13 (s, 2H); MS m/z 366.0 (M+H)+.

8-(6-Iodo-benzo[1,3]dioxol-5-ylsulfanyl)-9-(pent-4-ynyl)adenine: A solution of 7 (40 mg, 96.8 mol), Cs2CO3 (31.5 mg, 96.8 mol) and pent-4-ynyl tosylate (28 mg, 114 mol) in anhydrous DMF (1 mL) was stirred at 80° C. for 30 min. The solvent was removed under high vacuum and the crude purified by preparatory thin layer chromatography to give the desired product (25 mg, 53.9%): $^1$H NMR (400 MHz, CDC13/methanol-d4) 8.23 (s, 1H), 7.38 (s, 1H), 7.04 (s, 1H), 6.05 (s, 2H), 4.32 (t, J=7.3 Hz, 2H), 2.33-2.31 (m, 2H), 2.12-2.04 (m, 3H); 13C NMR (100 MHz, CDC13/methanol-d4) 151.1, 149.6, 149.2, 147.5, 125.7, 119.4, 113.6, 102.4, 93.8, 82.1, 69.4, 42.8, 28.1, 15.8; MS m/z 480.0 (M+H)+. HPLC: (a) 98.5% (65% water-35% acetonitrile); (b) 97.7% (35% to 95% acetonitrile).

3-(tert-Butoxycarbonyl-isopropyl-amino)-propyl tosylate: A solution of 3-bromo-1-propanol (5 g, 0.036 mol) in isopropylamine (9 mL, 0.11 mol) was heated overnight at 50° C. with stirring. Solvent was removed under vacuum to give the product, 3-isopropyl-amino-propanol as a white solid. To this were added di-tert-butyl dicarbonate (10 g, 0.05 mol) and triethylamine (11 mL, 0.08 mol) and the resulting solution stirred at room temperature overnight. Following solvent removal, the crude was purified by column chromatography on silica gel (CH2C12, then CH2C12: acetone at 3:1) to provide the 3-(tert-butoxycarbonyl-isopropyl-amino)-propanol (5.8 g, 75%). $^1$H NMR (400 MHz, CDC13) 3.93 (bs, 1H), 3.58 (m, 2H), 3.33 (m, 2H), 1.67 (m, 2H), 1.48 (s, 9H), 1.16 (d, J=6.9 Hz, 6H); MS m/z 218.1 (M+H)+. A solution of 3-(tert-butoxycarbonyl-isopropyl-amino)-propanol (3.5 g, 0.016 mol), p-toluenesulfonyl chloride (3.7 g, 0.019 mol) and pyridine (1.6 mL, 0.019 mol) in CH2C12 (50 mL) was stirred overnight at room temperature. Following solvent removal, the product (2.3 g, 40%) was isolated by column chromatography on silica gel (hexanes:CH2C12:EtOAc at 5:4:1). $^1$H NMR (400 MHz, CDC13) 7.79 (d, J=8.2 Hz, 2H,), 7.35 (d, J=8.2 Hz, 2H,), 4.06-4.03 (m, 3H), 3.09 (t, J=6.5 Hz, 2H), 2.45 (s, 3H), 1.91-1.87 (m, 2H), 1.42 (s, 9H), 1.08 (d, J=6.7 Hz, 6H); MS m/z 372.2 (M+H)+.

8-(6-Iodo-benzo[1,3]dioxol-5-yIsulfanyl)-9-(3-isopropylamino-propyl)adenine: A solution of 7 (125 mg, 303 mol), 3-(tert-butoxycarbonyl-isopropyl-amino)-propyl tosylate (269 mg, 726 mol), Cs2CO3 (99 mg, 303 mol) in anhydrous DMF (2 mL) was stirred at 80° C. for 24 h. The solvent was removed under vacuum and the crude purified by preparatory thin layer chromatography on silica gel (CHC13:MeOH:NH4OH at 10:1:0.5) to afford the 9N-alkylated compound. This was placed in TFA (1 mL) at 0° C. for 1.5 h to remove the Boc protecting group and yield 11 (30 mg, 19.3% yield): $^1$H NMR (400 MHz, CDC13) 8.31 (s, 1H), 7.29 (s, 1H), 6.88 (s, 1H), 6.10 (bs, 2H), 5.96 (s, 2H), 4.29 (t, J=7.0 Hz, 2H), 2.75-2.69 (m, 1H), 2.58 (t, J=6.8 Hz, 2H), 2.02-1.95 (m, 2H), 1.03 (d, J=6.2 Hz, 6H); 13C NMR (100 MHz, CDC13) 154.6, 152.9, 151.6, 149.2, 148.9, 146.2, 127.9, 120.1, 119.2, 112.2, 102.2, 91.1, 48.7, 43.9, 41.7, 30.3, 22.9; MS m/z 513.2 (M+H)+. HPLC: (a) 98.9% (65% water-35% acetonitrile); (b) 95.0% (20% to 40% acetonitrile).

8-(6-Bromo-benzo[1,3]dioxol-5-yIsulfanyl)-9-(3-isopropylamino-propyl)adenine: A solution of 8-(6-Bromo-benzo[1,3]dioxol-5-ylsulfanyl)adenine (513 mg, 1.4 mmol), PPh3 (808 mg, 3.08 mmol), 3-bromo-1-propanol (253 mg, 165 L, 1.82 mmol), DBAD (1612 mg, 7 mmol) in toluene (43.8 mL) and CH2C12 (8.75, mL) was stirred at room temperature for 20 min. The reaction mixture was loaded to a silica gel column (CHC1$_3$ then CHC1$_3$:EtOAc:hexanes: i-Propanol at 4:4:2:1) to provide the 9N-alkylated compound, 8-(6-bromo-benzo[1,3]dioxol-5-ylsulfanyl)-9-(3-bromo-propyl)adenine) (142.6 mg, 21% yield). A solution of this product (142.6 mg, 0.29 mmol) in 1,4-dioxane (12 mL) and i-propylamine (3 mL) was stirred at 100° C. for 2.5 h. The solvent was removed under vacuum and the crude purified by preparatory thin layer chromatography on silica gel (CHC13:MeOH:NH4OH at 10:1:0.5 then EtOAc:CH2C12:MeOH at 2:2:1) to afford 12 (51 mg, 8% yield). $^1$H NMR (400 MHz, CDC13) 8.30 (s, 1H), 7.04 (s, 1H), 6.81 (s, 1H), 6.48 (bs, 2H), 5.94 (s, 2H), 4.29 (t, J=7.0 Hz, 2H,), 2.74-2.68 (m, 1H), 2.57 (t, J=6.8 Hz, 2H,), 2.02-1.95 (m, 2H), 1.02 (d, J=6.0 Hz, 6H). 13C NMR (100 MHz, CDC13) 154.8, 152.9, 151.5, 148.8, 148.0, 145.2, 123.8, 120.0, 116.7, 113.2, 112.2, 102.3, 48.6, 43.8, 41.7, 30.2, 22.8; MS m/z 465.0 (M+H)+. HPLC: (a) 99.1% (65% water-35% acetonitrile); (b) 98.0% (20% to 40% acetonitrile).

8-Benzo[1,3]dioxol-5-ylmethyl-2-fluoroadenine: To a cooled (0° C.) solution of 16 (1.48 g, 5.2 mmol) in HF/pyridine (3.64 mL), NaNO2 (0.47 g, 6.76 mmol) was slowly added. The reaction was brought to room temperature, and further stirred for 1 h. Following dilution with CH$_2$Cl$_2$ (38 mL), the excess HF was quenched by stirring for an additional 1 h with CaCO3 (0.95 g) and water (5 mL). The mixture was dried in vacuo and subsequently purified by silica gel column chromatography (CHC13:MeOH:NH4OH at 5:1:0.5) to yield 17 (0.9 g, 60% yield). $^1$H NMR (400 MHz, DMSO-d6) 7.59 (bs, 2H), 6.94-6.90 (m, 3H), 6.81 (d, J=8.0 Hz, 1H), 6.03 (s, 2H), 4.06 (s, 2H); MS m/z 288.0 (M+H)+.

2-Fluoro-8-(6-iodo-benzo[1,3]dioxol-5-ylmethyl)adenine: A solution of 8-Benzo[1,3]dioxol-5-ylmethyl-2-fluoroadenine (50 mg, 0.17 mmol), NIS (94 mg, 0.4 mmol), TFA (20 mg, 13.4 L, 0.17 mmol) in CH2C12 (200 L) was stirred at room temperature overnight. After solvent removal, the desired product 18 (6 mg, 8.5%) was purified by silica gel column chromatography (CHC13:EtOAc at 9:1 to 4:6). $^1$H NMR (400 MHz, DMSO-d6) 7.6 (bs, 2H), 7.38 (s, 1H), 6.95 (s, 1H), 6.03 (s, 2H), 4.12 (s, 2H); MS m/z 414.1 (M+H)+.

2-Fluoro-8-(6-bromo-benzo[1,3]dioxol-5-ylmethyl)adenine: A solution of 8-Benzo[1,3]dioxol-5-ylmethyl-2-fluoroadenine (45 mg, 0.157 mmol), NBS (56 mg, 0.314 mmol) in DMF (0.5 mL) was stirred at room temperature for 1.5 h. Following solvent removal, product (20 mg, 34.8%) was collected through silica gel column purification (CHC13:EtOAc at 9:1 to 4:6). $^1$H NMR (400 MHz, acetone-d6) 7.51 (bs, 2H), 7.21 (s, 1H), 6.98 (s, 1H), 6.06 (s, 2H), 4.13 (s, 2H); MS m/z 366.0 (M+H)+.

2-Fluoro-8-(6-chloro-benzo[1,3]dioxol-5-ylmethyl)adenine: A solution of 8-Benzo[1,3]dioxol-5-ylmethyl-2-fluoroadenine (20 mg, 0.07 mmol), NCS (35.6 mg, 0.27 mmol) in anhydrous DMF (0.4 mL) was stirred at room temperature for 2.5 h. Following solvent removal, the product (11 mg, 48.8%) was collected through silica gel column purification (CHC13:EtOAc at 9:1 to 5:5). $^1$H NMR (400 MHz, DMSO-d6) 7.40 (bs, 2H), 6.97 (s, 1H), 6.89 (s, 2H), 5.97 (s, 2H), 4.04 (s, 2H); MS m/z 322.1 (M+H)+.

2-Fluoro-8-(6-iodo-benzo[1,3]dioxol-5-yïmethyl)-9-(pent-4-ynyl)adenine: A solution of 2-Fluoro-8-(6-iodo-benzo[1,3]dioxol-5-ylmethyl)adenine (6 mg, 0.0145 mmol), Cs2CO3 (5 mg, 0.0145 mmol) and pent-4-ynyl tosylate (4.5 mg, 0.189 mmol) in anhydrous DMF (200 L) was stirred at 60° C. for 1.5 h. Following solvent removal, product (5.9 mg, 84.9%) was collected through silica gel column purification (EtOAc:hexanes:CHC13:i-PrOH at 10:20:20:1). $^1$H NMR (400 MHz, CDC13) 7.29 (s, 1H), 6.59 (s, 1H), 5.94 (s, 2H), 5.83 (bs, 2H), 4.26 (s, 2H), 4.11 (t, J=7.4 Hz, 2H), 2.26-2.19 (m, 2H), 2.00 (t, J=2.5 Hz, 1H), 1.98-1.94 (m, 2H); 13C NMR (lOO MHZ, CDC13) 150.9, 148.9, 147.8, 131.5, 118.8, 109.4, 101.9, 88.1, 82.3, 69.9, 42.3, 39.2, 28.2, 15.9; MS m/z 480.0 (M+H)+. HPLC: (a) 95.5% (60% water-40% acetonitrile); (b) 95.0% (35% to 55% acetonitrile).

2-Fluoro-8-(6-bromo-benzo[1,3]dioxol-5-ylmethyl)-9-(pent-4-ynyl)adenine: A solution of 2-Fluoro-8-(6-bromo-benzo[1,3]dioxol-5-ylmethyl)adenine (20 mg, 55 mol), Cs2CO3 (18 mg, 55 mol) and pent-4-ynyl tosylate (17 mg, 72 mol) in anhydrous DMF (138 L) was stirred at 60° C. for 2 h. Following solvent removal, the product (13 mg, 54.7%) was collected through silica gel column purification (EtOAc:hexanes:CHC13:i~PrOH at 10:20:20:1). $^1$H NMR (400 MHz, CDC13) 7.05 (s, 1H), 6.60 (s, 1H), 6.15 (bs, 2H), 5.96 (s, 2H), 4.28 (s, 2H), 4.13 (t, J=7.5 Hz, 2H), 2.25-2.21 (m, 2H), 2.00 (t, J=2.6 Hz, 1H), 1.98-1.92 (m, 2H); 13C NMR (100 MHz, CDC13) 157.6, 156.0, 152.6, 150.2, 147.5, 127.6, 116.4, 114.1, 112.5, 109.5, 101.6, 81.9, 69.5, 41.9, 33.7, 27.8, 15.5; MS m/z 432.0 (M+H)+. HPLC: (a) 99.0% (60% water-40% acetonitrile); (b) 98.5% (35% to 55% acetonitrile).

2-Fluoro-8-(6-chloro-benzo[1,3]dioxol-5-ylmethyl)-9-(pent-4-ynyl)adenine: A solution of 2-Fluoro-8-(6-chloro-benzo[1,3]dioxol-5-ylmethyl)adenine (11 mg, 0.034 mmol), Cs2CO3 (11 mg, 0.034 mmol) and pent-4-ynyl tosylate (10.5 mg, 0.044 mmol) in anhydrous DMF (85 L) was stirred at 50° C. for 1 h. Following solvent removal, the product (4.2 mg, 31.9%) was collected through silica gel column purification (EtOAc:hexanes:CHC13:i-PrOH at 10:20:20:1). $^1$H NMR (400 MHz, CDC13) 6.89 (s, 1H), 6.61 (s, 1H), 5.98 (bs, 2H), 5.96 (s, 2H), 4.27 (s, 2H), 4.13 (t, J=7.5 Hz, 2H), 2.24-2.10 (m, 2H), 2.00-1.91 (m, 3H); 13C NMR (100 MHz, CDC13) 1597, 158.0, 156.3, 150.6, 147.7, 147.2, 126.2, 125.3, 110.0, 102.0, 82.3, 69.9, 42.2, 31.4, 28.1, 15.8; MS m/z 388.1 (M+H)+. HPLC: (a) 98.1% (65% water-35% acetonitrile); (b) 97.0% (35% to 45% acetonitrile).

2-Fluoro-8-(6-iodo-benzo[1,3]dioxol-5-ylmethyl)-9-(3-isopropylamino-propyl)adenine: A solution of 2-Fluoro-8-(6-iodo-benzo[1,3]dioxol-5-ylmethyl)adenine (300 mg, 0.726 mmol), Cs2CO3 (285 mg, 0.87 mmol) and 1,3-dibromopropane (370 L, 3.63 mmol) in anhydrous DMF (5 mL) was stirred at 50° C. for 2 h. Following solvent removal, product (330 mg, 85%) was collected through silica gel column purification (CHC13 then EtOAc:hexanes:CHC13:i-PrOH at 4:2:4:0.4). MS m/z 534.0 (M+H)+. To this product, i-PrNH2 (10 mL) was added in excess and the resulting solution stirred at room temperature for 1 h. Excess amine was removed and product (230 mg, 75%) collected through silica gel column purification (CHC13:EtOAc:i-PrOH: NH4OH at 4:4:2:0.3). $^1$H NMR (400 MHz, CDC13) 7.29 (s, 1H), 6.59 (s, 1H), 5.94 (s, 2H), 5.89 (bs, 2H), 4.25 (s, 2H), 4.11 (t, J=7.0 Hz, 2H), 2.73-2.60 (m, 1H), 2.55 (t, J=6.8 Hz, 1H), 1.93-1.86 (m, 2H), 1.03-1.02 (d, J=6.0 Hz, 6H); 13C NMR (100 MHz, methanol-d4) 160.0, 158.4, 157.2, 152.4, 151.3, 149.4, 148.4, 133.1, 118.7, 110.6, 102.4, 88.5, 42.8, 40.1, 38.8, 27.6, 19.4; MS m/z 513.2 (M+H)+. HPLC: (a) 98.5% (60% water-40% acetonitrile); (b) 97.2% (20% to 50% acetonitrile).

2-Fluoro-8-(3,4-dimethoxy-benzyl)adenine: Starting from 2-amino-8-(3,4-dimethoxy-benzyl) adenine (0.66 g, 2.2 mmol) and following the procedure for the synthesis of 17, the desired product was obtained (0.34 g, 51%). $^1$H NMR (400 MHz, DMSO-d6) 7.61 (bs, 2H), 7.03 (s, 1H), 6.94 (d, J=8.3 Hz, 1H), 6.84 (d, J=8.6 Hz, 1H), 4.07 (s, 2H), 3.80 (s, 3H), 3.77 (s, 3H); MS m/z 304.0 (M+H)+.

2-Fluoro-8-(2-iodo-4,5-dimethoxy-benzyl)adenine: A solution of 2-Fluoro-8-(3,4-dimethoxy-benzyl)adenine (50 mg, 0.165 mmol), NIS (74 mg, 0.33 mmol), TFA (18.8 mg, 12.7 L, 0.165 mmol) in acetonitrile (120 L) was stirred at room temperature for 24 h. Following solvent removal, the product (12 mg, 16.9%) was collected through silica gel column purification (CHC13:MeOH:AcOH at 80:1:0.5 to 30:1:0.5). MS m/z 430.1 (M+H)+.

2-Fluoro-8-(2-bromo-4,5-dimethoxy-benzyl)adenine (29): A solution of 27 (65 mg, 0.226 mmol), NBS (80 mg, 0.45 mmol) in DMF (0.75 mL) was stirred at room temperature for 2.5 h. Following solvent removal, the product (8.2 mg, 53.6%) was collected through silica gel column purification (CHC13:MeOH:AcOH at 80:1:0.5 to 30:1:0.5). $^1$H NMR (400 MHz, aceton-d6) 7.13 (s, 1H), 7.09 (s, 1H), 6.80 (bs, 2H), 4.26 (s, 2H), 3.84 (s, 3H), 3.78 (s, 3H); MS m/z 382.0 (M+H)+.

2-Fluoro-8-(2-chloro-4,5-dimethoxy-benzyl)adenine: A solution of 2-Fluoro-8-(3,4-dimethoxy-benzyl)adenine (40 mg, 0.132 mmol), NCS (77.8 mg, 0.58 mmol) in anhydrous DMF (0.7 mL) was stirred at room temperature for 5.5 h. Following solvent removal, the product (22 mg, 49.4%) was collected through silica gel column purification (CHC13: EtOAc at 8:2 to 4:6). MS m/z 338.0 (M+H)+.

2-Fluoro-8-(2-iodo-4,5-dimethoxy-benzyl)-9-(pent-4-ynyl)adenine: A solution of 2-fluoro-8-(2-iodo-4,5-dimethoxy-benzyl)adenine (12 mg, 0.028 mmol), Cs2CO3 (9 mg, 0.028 mmol), pent-4-ynyl tosylate (8.6 mg, 7 L, 0.036 mmol) in anhydrous DMF (80 L) was stirred at 50° C. for 1 h. Following solvent removal, the product (13.7 mg, 99%) was collected through silica gel column purification (CHC13:EtOAc:hexanes:i-PrOH at 20:10:20:1). $^1$H NMR (400 MHz, CDC13) 7.27 (s, 1H), 6.65 (s, 1H), 5.94 (bs, 2H), 4.29 (s, 2H), 4.13 (t, J=7.3 Hz, 2H), 3.87 (s, 3H), 3.73 (s, 3H), 2.26-2.22 (m, 2H), 2.00 (t, J=2.6 Hz, 1H), 1.97-1.90 (m, 2H); 13C NMR (100 MHz, CDC13) 156.5, 153.2, 151.3, 150.0, 149.1, 130.9, 121.9, 112.6, 88.5, 82.5, 70.0, 56.4, 56.2, 42.6, 39.2, 28.4, 16.1; MS m/z 496.2 (M+H)+. HPLC: (a) 99.9% (60% water-40% acetonitrile); (b) 96.8% (35% to 55% acetonitrile).

2-Fluoro-8-(2-bromo-4,5-dimethoxy-benzyl)-9-(pent-4-ynyl)adenine: A solution of 8-(2-bromo-4,5-dimethoxy-benzyl)-2-fluoroadenine (13 mg, 0.034 mmol), Cs2CO3 (11 mg, 0.034 mmol), pent-4-ynyl tosylate (10 mg, 9 L, 0.044 mmol) in anhydrous DMF (80 L) was stirred at 60° C. for 30 min. Following solvent removal, the product (8.2 mg, 53.6%) was collected through silica gel column purification (CHC13:EtOAc:hexanes:i-PrOH at 20:10:20:1). $^1$HNMR (400 MHz, CDC13) 7.06 (s, 1H), 6.67 (s, 1H), 5.92 (bs, 2H), 4.31 (s, 2H), 4.14 (t, J=7.4 Hz, 2H), 3.88 (s, 3H), 3.75 (s, 3H), 2.25-2.20 (m, 2H), 1.99 (t, J=2.6 Hz, 1H), 1.96-1.89 (m, 2H); 13C NMR (100 MHz, CDC13) 160.0, 158.3, 156.7, 153.4, 151.3, 149.4, 127.2, 117.3, 115.9, 114.5, 113.2, 82.7, 70.2, 56.62, 56.56, 42.7, 34.3, 30.1, 28.5, 16.3; MS m/z 447.9 (M+H)+. HPLC: (a) 99.0% (60% water-40% acetonitrile); (b) 98.8% (35% to 55% acetonitrile).

2-Fluoro-8-(2-chloro-4,5-dimethoxy-benzyl)-9-(pent-4-ynyl)adenine: A solution of 8-(2-chloro-4,5-dimethoxy-benzyl)-2-fluoroadenine (22 mg, 0.065 mmol), Cs2CO3 (21 mg, 0.065 mmol), pent-4-ynyl tosylate (20 mg, 17.3 L, 0.085 mmol) in anhydrous DMF (170 L) was stirred at 50° C. for 2 h. Following solvent removal, the product (14 mg, 53.8%) was collected through silica gel column purification (CHC13:EtOAc:hexanes:i-PrOH at 20:10:20:1). $^1$H NMR (400 MHz, CDC13) 6.91 (s, 1H), 6.67 (s, 1H), 6.01 (bs, 2H), 4.31 (s, 2H), 4.14 (t, J=7.5 Hz, 2H), 3.87 (s, 3H), 3.75 (s, 3H), 2.24-2.20 (m, 2H), 2.01-1.99 (m, 1H), 1.97-1.88 (m, 2H); 13C NMR (100 MHz, CDC13) 1596, 157.9, 156.3, 152.3, 148.9, 146.0, 124.9, 112.7, 82.3, 69.9, 56.3, 56.2, 42.2, 31.2, 28.1, 15.9; MS m/z 404.1 (M+H)+. HPLC: (a) 95.1% (65% water-35% acetonitrile); (b) 96.7% (35% to 45% acetonitrile).

Radiolabeling of Examples 8 and 9

Ten microliters of [$^{131}$I]-NaI (3mCi) in 0.1 M NaOH is added to a 0.3 mL ReactiVial followed by 5 μL of a 5 μg/ptL methanol solution of 2-fluoro-9-[3-(N—N-tert-butoxycarboxy-2-propylamino) propyl]-8-(4-trimethylstannyl-1,3-benzodioxol-5-yl)methyl adenine followed by 10 μL of Chloramine-T (CAT) in acetic acid (0.5 mg/mL). The reaction mixture is vortexed and kept at 50° C. for 5 minutes. 10 μL 6M HCl is added, the reaction mixture is vortexed and kept at 50° C. for 15 minutes. 6/xL 1 OM NaOH is added, the reaction mixture is vortexed and injected into a HPLC (Phenomenex Luna Cl 8 column (5 μm, 4.4×250 mm) Both columns were eluted at 1 mL/min with a solvent gradient of 0.1% TFA to 0.1% TF A/70% acetonitrile over 15 minutes. The PU-DZ8 fraction is collected, dried at 50° C. by a stream of nitrogen, reconstituted in saline and sterile filtered to yield ~90% radiochemical yield of [$^{131}$I]-Compound 8. [$^{124}$I]-Compound 8 and [$^{131}$I]-Compound 9 are produced in an analogous manner.

Binding Studies

CWR22-rvl prostate cancer cells are grown in RMPI 1640 media supplemented with 10% fetal bovine serum at 37° C. The cells are removed from the flasks using trypsin and propagated with a 1:6 subculture ratio.

Displacement Binding Studies

Figure 11:
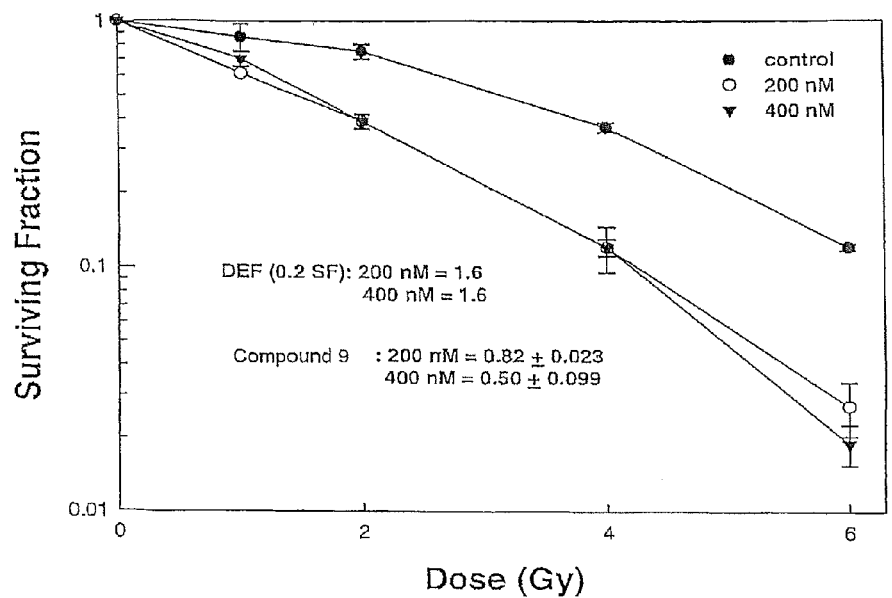
FIGS. 11 A and B show enhancement of radiation sensitivity in glioma cells after pretreatment with to Compounds 9 or 8, respectively.
Figure 11B:
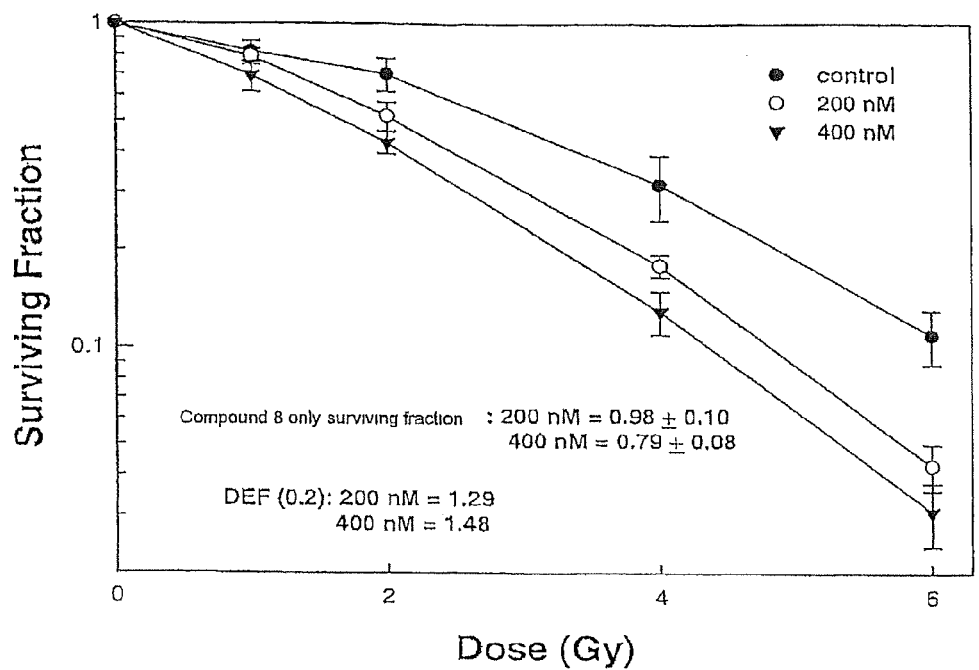

Displacement studies are performed with [$^{131}$I]-Compound 8 and CWR22-rvl prostate cancer cells. Briefly, triplicate samples of cells are mixed with <1 nM of radioligand and increasing amounts of a cold competitor (1 pM to 1 μM Compound 8 or 9). The solutions are shaken on an orbital shaker and after 60 minutes the cells are isolated and washed with ice cold Tris buffered saline using a Brandel cell harvester. AU the isolated cell samples are counted and the specific uptake of [$^{131}$I]-Compound 8 determined. These data are plotted against the concentration of the cold competitor to give sigmoidal displacement curves. The $IC_{50}$ values are determined using a one site model and a least squares curve fitting routine. The displacement binding of [$^{131}$I]-Compound 8 is determined in an analogous manner FIG. 11 shows example displacement curves for and [$^{131}$I]-Compound 8 and [$^{131}$I]-Compound 9.

Saturation Binding Studies

Figure 12:
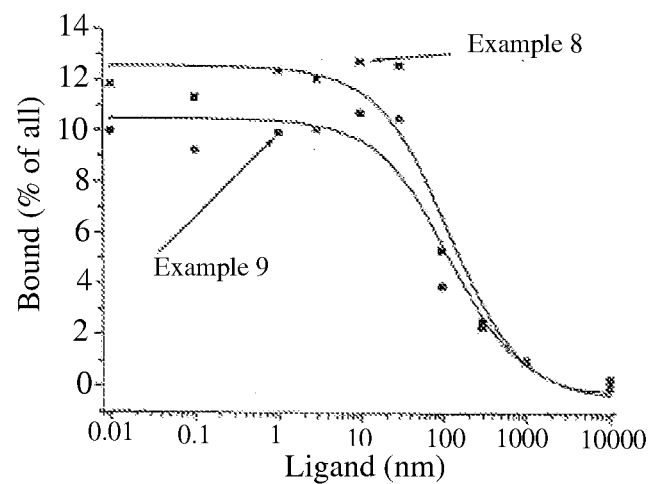
FIG. 12 shows example displacement curves for [$^{131}$I]-Compound 9 and [$^{131}$I]-Compound 9.

Saturation studies are performed with [$^{131}$I]-Compound 8 and CWR22-rvl prostate cancer cells. Briefly, triplicate samples of cells are mixed with increasing amount of 131I-DZ8 either with or without 1 μM unlabeled Compound 9. The solutions are shaken on an orbital shaker and after 60 minutes the cells are isolated and washed with ice cold Tris buffered saline using a Brandel cell harvester. AU the isolated cell samples are counted and the specific uptake of $^{131}$I-Compound 8 determined. These data are plotted against the concentration of $^{131}$I-Compound to give a saturation binding curve. The Bmax (maximal binding) and Kd (binding affinity) are determined by using a least squares curve fitting routine. The saturation binding of [$^{131}$I]-Compound 9 is determined in an analogous manner. FIG. 12 shows example saturation curves for [$^{131}$]-Compound 8 and [$^{131}$I]-Compound 9.

Animal Studies

[$^{131}$I]-Compound 8 and [$^{131}$I]-Compound 9 biodistribution was studied in an animal model of prostate cancer. CWR22 tumors are grown in athymic mice supplemented with a testosterone pellet (12.5 mg pellet, Innovative Research of America, Sarasota, Fla.). Once the tumors are 500 mg in size the pellet is removed and the mice castrated.

Figure 13:
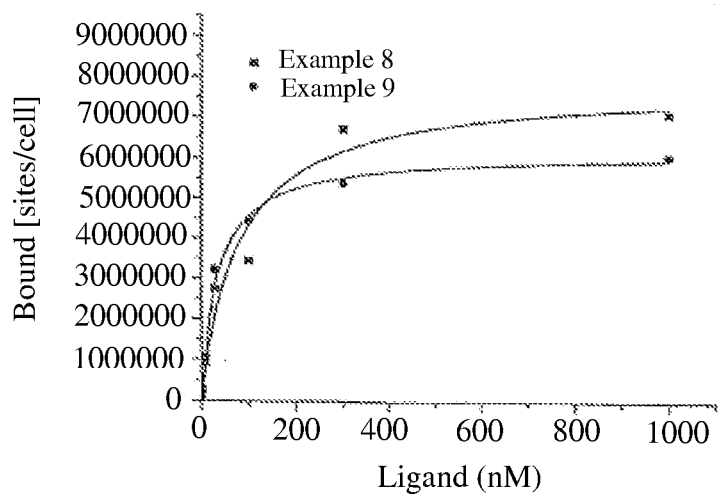
FIG. 13 shows saturation curves [$^{131}$I]-Compound 8 and [$^{131}$I]-Compound 9.
Figure 14:
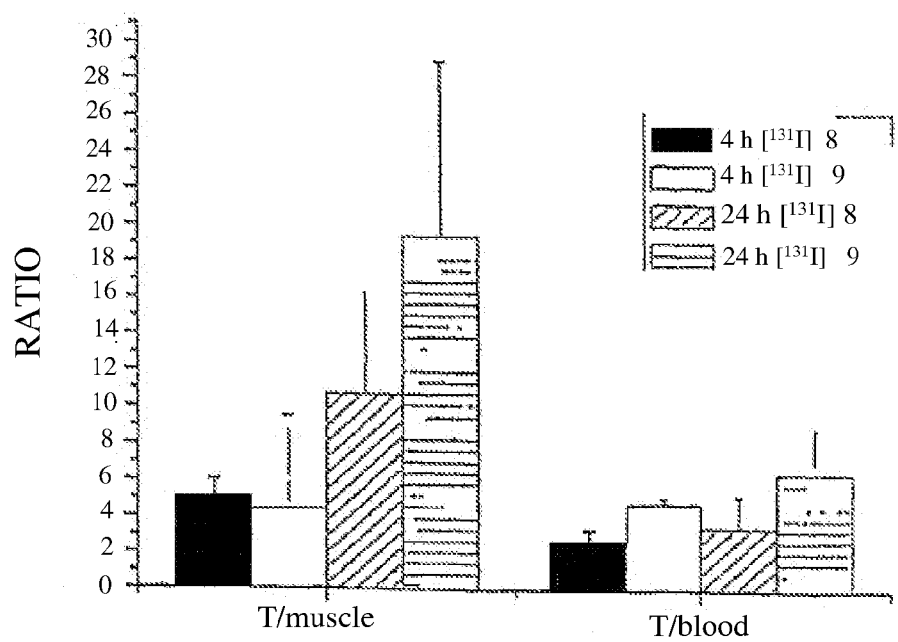
FIG. 14 shows the ratio of [$^{131}$I]-Compound 8 and [$^{131}$I]-Compound 9 in tumor and muscle and tumor and blood 4 and 24 hours after administration.

Two groups of eight mice were injected at 3 days post castration, with 10 μCi of [$^{131}$I]-Compound 8 or [$^{131}$I]-Compound 9. These mice were sacrificed at either 4 or 24 hours post injection and the organs of interest removed, weighed and counted in a gamma counter with a standard of 10% of the [$^{131}$I]-Compound 8 injected dose. The data were then expressed as a % of the injected dose per gram of tissue (% ID/g). FIG. 13 shows the tumor/non-tumor uptake ratios for selected organs. As shown, there is a substantial excess of accumulation of the radiolabeled compound in tumor as compared to both muscle and blood, and this ratio increases over time.

In a second study, 14 mice were injected with [$^{131}$I]-Compound 9 with increasing amounts of unlabeled Compound 9. The mice were sacrificed at 4 h p.i. and tissue analyzed as described above. While the addition of 2 or 18 nanomoles of unlabeled Compound 9 decreased the amount of captured label to some extent, it did not alter the tissue distribution to any significant extent.

In a third study a single mouse was injected with [124I]-Compound 8 and imaged with a microPET at around 3 and 17 hours post injection. The area of the tumor was plainly visible in the images obtained, along with residual activity in the large intestine.

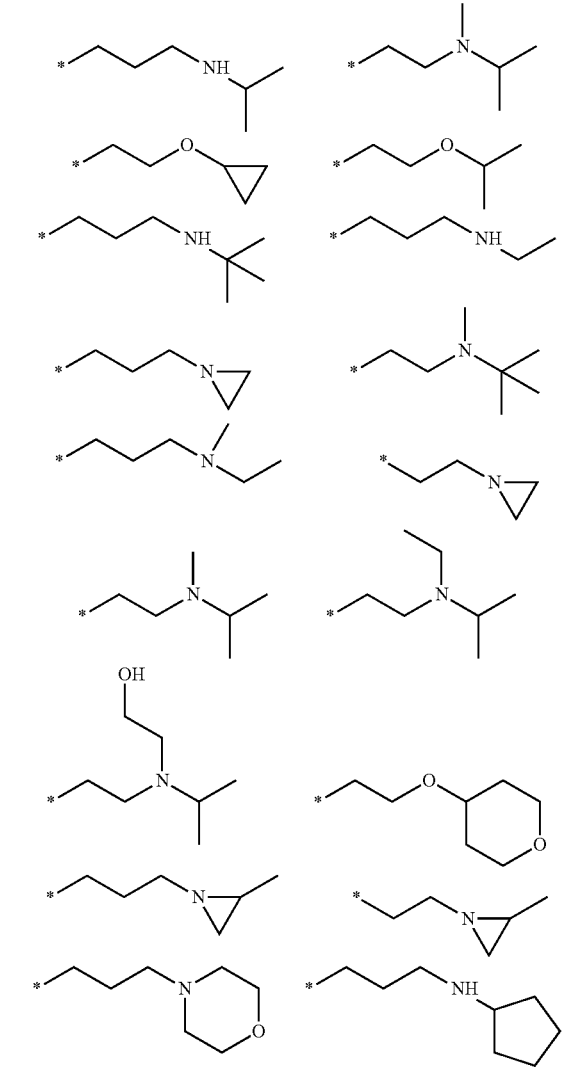

-continued
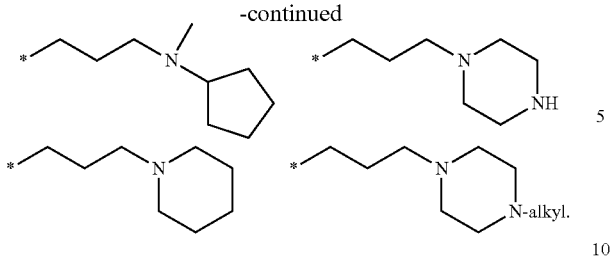

What is claimed is:

1. A compound of the formula:

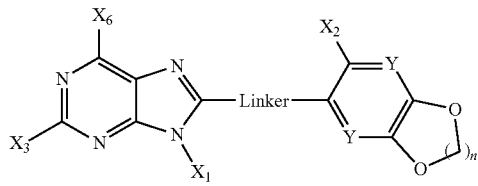

wherein:
$X_6$ is $NH_2$;
$X_3$ is hydrogen or halogen;
$X_1$ is a $C_1$ to $C_{10}$ alkyl, alkenyl, or alkynyl group, wherein the alkyl, alkenyl, or alkynyl group includes a heteroatom;
the linker is selected from the group consisting of $CH_2$, O, NH and S;
Y is independently CH or N;
$X_2$ is halogen, alkyl, alkoxy, halogenated alkoxy, hydroxyalkyl, pyrollyl, optionally substituted aryloxy, alkylamino, dialkylamino, carbamyl, amido, alkylamido dialkylamido, acylamino, alkylsulfonylamido, trihalomethoxy, trihalocarbon, thioalkyl, COO-alkyl, $NH_2$, OH, CN, $SO_2X_7$, $NO_2$, NO, C=$SR_2$, $NHSO_2X_7$, C=$OR_2$ where $X_7$ is F, $NH_2$, alkyl or H, and $R_2$ is alkyl, $NH_2$, NH-alkyl or O-alkyl; and
n is 1 or 2,
or a pharmaceutically acceptable salt thereof.

2. The compound of claim 1, wherein $X_2$ is $NH_2$, alkylamino or dialkylamino.

3. The compound of claim 1, wherein $X_1$ is an amino alkyl moiety, optionally substituted on the amino nitrogen with one or two carbon-containing substituents selected independently from the group consisting of alkyl, alkenyl and alkynyl substituents, wherein the total number of carbons in the amino alkyl moiety is from 1 to 10.

4. The compound of claim 3, wherein $X_1$ includes a cyclic portion.

5. The compound of claim 4, wherein the cyclic portion includes at least one nitrogen.

6. The compound of claim 3, wherein the linker is S.

7. The compound of claim 6, wherein $X_1$ includes a cyclic portion.

8. The compound of claim 7, wherein the cyclic portion includes at least one nitrogen.

9. The compound of claim 1, wherein $X_1$ contains at least one nitrogen heteroatom.

10. The compound of claim 1, wherein $X_1$ contains at least one oxygen heteroatom.

11. The compound of claim 1, wherein $X_1$ includes a cyclic portion.

12. The compound of claim 11, wherein the cyclic portion includes at least one heteroatom.

13. The compound of claim 11, wherein the cyclic portion is a 6-membered ring.

14. The compound of claim 11, wherein the cyclic portion is a 3-membered ring.

15. The compound of claim 1, wherein the linker is $CH_2$.

16. The compound of claim 15, wherein $X_2$ is $NH_2$, alkylamino or dialkylamino.

17. The compound of claim 16, wherein $X_1$ is an amino alkyl moiety, optionally substituted on the amino nitrogen with one or two carbon-containing substituents selected independently from the group consisting of alkyl, alkenyl and alkynyl substituents, wherein the total number of carbons in the amino alkyl moiety is from 1 to 10.

18. The compound of claim 17, wherein $X_1$ includes a cyclic portion.

19. The compound of claim 18, wherein the cyclic portion includes at least one nitrogen.

20. The compound of claim 1, wherein the linker is S.

21. The compound of claim 20, wherein $X_1$ includes a cyclic portion.

22. The compound of claim 21, wherein the cyclic portion include at least one nitrogen.

23. The compound of claim 1, wherein $X_1$ comprises a secondary or tertiary amine forming a 6-membered ring with the nitrogen.

24. The compound of claim 1, wherein $X_1$ is —$(CH_2)_n$—N—$R_{10}R_{11}$, wherein n is 2 or 3 and $R_{10}$ and $R_{11}$ are independently selected from hydrogen, methyl, ethyl, ethene, ethyne, propyl, isopropyl, isobutyl, ethoxy, cyclopentyl, an alkyl group forming a 3 or 6-membered ring including the N, or a secondary or tertiary amine forming a 6-membered ring with the nitrogen.

25. The compound of claim 1, wherein $X_1$ is selected from the following:

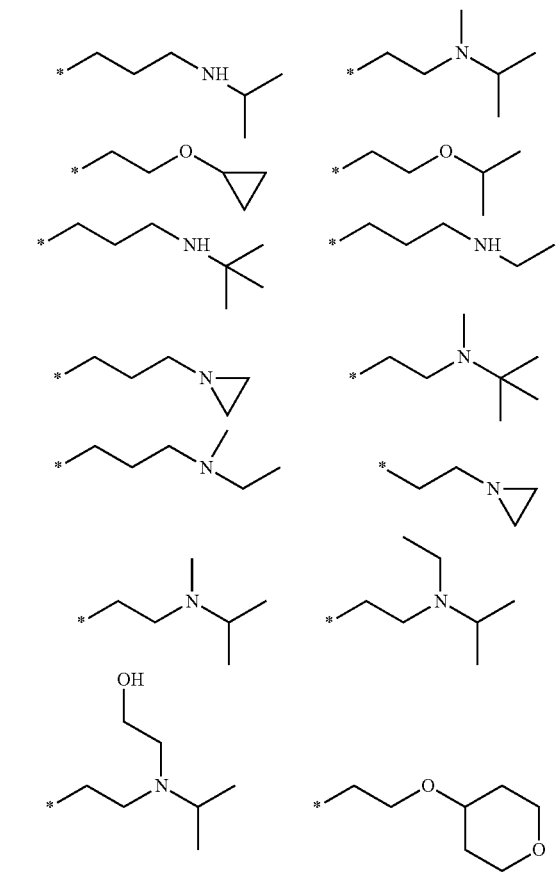

-continued

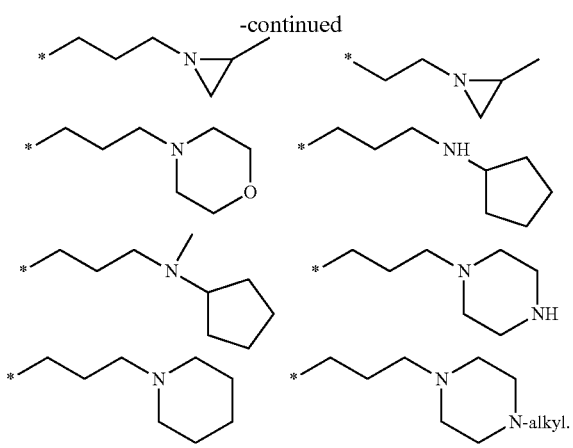

26. A compound of the formula:

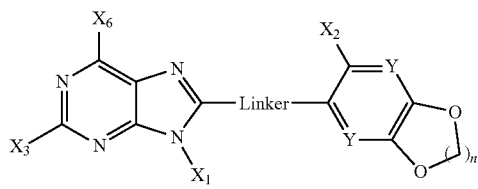

wherein:
X₆ is NH₂;
X₃ is hydrogen or halogen;
X₁ is hydrogen or a C1 to C10 alkyl, alkenyl, or alkynyl group, optionally including a heteroatom;
the linker is selected from the group consisting of CH₂, O, NH and S;
Y is independently CH or N;
X₂ is alkyl, alkoxy, halogenated alkoxy, hydroxyalkyl, pyrollyl, optionally substituted aryloxy, alkylamino, dialkylamino, carbamyl, amido, alkylamido dialkylamido, acylamino, alkylsulfonylamido, trihalomethoxy, trihalocarbon, thioalkyl, COO-alkyl, NH₂, OH, CN, SO₂X₇, NO₂, NO, C=SR₂, NHSO₂X₇, C=OR₂ where X₇ is F, NH₂, alkyl or H, and R₂ is alkyl, NH₂, NH-alkyl or O-alkyl; and
n is 1 or 2,
or a pharmaceutically acceptable salt thereof.

27. The compound of claim 26, wherein X₂ is NH₂, alkylamino or dialkylamino.

28. The compound of claim 26, wherein X₁ includes a cyclic portion which optionally includes at least one heteroatom.

29. The compound of claim 26, wherein the linker is CH₂.

30. The compound of claim 29, wherein X₁ includes a cyclic portion which optionally includes at least one nitrogen.

31. The compound of claim 26, wherein the linker is S.

32. The compound of claim 31, wherein X₁ includes a cyclic portion which optionally includes at least one nitrogen.

33. The compound of claim 30, wherein the cyclic portion is a 6-membered ring or a 3-membered ring.

34. The compound of claim 32, wherein the cyclic portion is a 6-membered ring or a 3-membered ring.

35. The compound of claim 1, wherein X₂ is halogen.

36. The compound of claim 35, wherein X₁ is —(CH₂)ₙ—N—R₁₀R₁₁, wherein n is 2 or 3 and R₁₀ and R₁₁ are independently selected from hydrogen, methyl, ethyl, ethene, ethyne, propyl, isopropyl, isobutyl, ethoxy, cyclopentyl, an alkyl group forming a 3 or 6-membered ring including the N, or a secondary or tertiary amine forming a 6-membered ring with the nitrogen.

37. The compound of claim 36, wherein the linker is S.

38. The compound of claim 37, wherein X₁ includes a cyclic portion.

39. The compound of claim 38, wherein the cyclic portion includes at least one nitrogen.

40. The compound of claim 38, wherein the cyclic portion is a 6-membered ring or 3-membered ring.

41. The compound of claim 36, wherein the linker is CH₂.

42. The compound of claim 41, wherein X₁ includes a cyclic portion.

43. The compound of claim 42, wherein the cyclic portion includes at least one nitrogen.

44. The compound of claim 42, wherein the cyclic portion is a 6-membered ring or 3-membered ring.

45. The compound of claim 35, wherein X₁ is selected from the following: